United States Patent
Nachtomy et al.

[11] Patent Number: 6,152,878
[45] Date of Patent: Nov. 28, 2000

[54] INTRAVASCULAR ULTRASOUND ENHANCED IMAGE AND SIGNAL PROCESSING

[75] Inventors: Ehud Nachtomy, Givataim; Jacob Richter, Ramat Hasharon, both of Israel

[73] Assignee: Medinol Ltd., Tel Aviv, Israel

[21] Appl. No.: 09/088,314

[22] Filed: Jun. 1, 1998

Related U.S. Application Data

[62] Division of application No. 08/879,125, Jun. 19, 1997.

[51] Int. Cl.$^7$ ....................................................... A61B 8/12
[52] U.S. Cl. .............................................................. 600/467
[58] Field of Search ...................................... 600/437, 443, 600/447, 462–463, 466–467, 471; 125/916

[56] References Cited

U.S. PATENT DOCUMENTS

| | | |
|---|---|---|
| 4,063,549 | 12/1977 | Beretsky et al. . |
| 4,164,728 | 8/1979 | Marsh . |
| 4,794,931 | 1/1989 | Yock . |
| 4,803,990 | 2/1989 | Bonnefous et al. . |
| 4,951,677 | 8/1990 | Crowley et al. . |
| 5,000,185 | 3/1991 | Yock . |
| 5,040,225 | 8/1991 | Gouge . |
| 5,217,456 | 6/1993 | Narcisco, Jr. . |
| 5,257,629 | 11/1993 | Kitney et al. ............................ 600/467 |
| 5,299,576 | 4/1994 | Shiba . |
| 5,313,949 | 5/1994 | Yock . |
| 5,331,964 | 7/1994 | Trahey et al. . |
| 5,353,798 | 10/1994 | Sieben . |
| 5,363,849 | 11/1994 | Suorsa et al. . |
| 5,363,850 | 11/1994 | Soni et al. . |
| 5,419,328 | 5/1995 | Goh et al. . |
| 5,445,155 | 8/1995 | Sieben . |
| 5,452,448 | 9/1995 | Narcisco, Jr. . |
| 5,453,575 | 9/1995 | O'Donnell et al. ...................... 600/468 |
| 5,476,096 | 12/1995 | Olstad et al. . |
| 5,503,153 | 4/1996 | Liu et al. . |
| 5,515,849 | 5/1996 | Murashita et al. . |
| 5,520,185 | 5/1996 | Soni et al. . |
| 5,522,392 | 6/1996 | Soursa et al. . |

(List continued on next page.)

FOREIGN PATENT DOCUMENTS 4-146737  5/1992  Japan .

OTHER PUBLICATIONS

K. M. Coy et al., "Intravascular Ultrasound Imaging: A Current Perspective", JACC vol. 18, No. 7, Dec. 1991: 1811–23.

N. Bom et al., "Early and Recent Intraluminal Ultrasound Devices", Intl. Journal of Cardiac Imaging 4: 79–88, 1989.

L.K. Ryan; et al., A High Frequency Intravascular Ultrasound Imaging System for Investigation of Vessel Wall Properties, IEEE 1992 Ultrasonics Syposium, 1101–1105.

A. Gronningsaeter et al., "Vessel Wall Detection and Blood Noise Reduction in Intravascular Ultrasound Imaging", IEEE Transactions on Ultrasonics, Ferroelectrics, and Frequency Control, vol. 43, No. 3 May 1996, pp. 359–369.

(List continued on next page.)

Primary Examiner—Francis J. Jaworski
Attorney, Agent, or Firm—Kenyon & Kenyon

[57] ABSTRACT

A device and method for intravascular ultrasound imaging. A catheter including ultrasonic apparatus is introduced into and may be moved through a bodily lumen. The apparatus transmits ultrasonic signals and detects reflected ultrasound signals which contain information relating to the bodily lumen. A processor coupled to the catheter is programmed to derive a first image or series of images and a second image or series of images from the detected ultrasound signals. The processor is also programmed to compare the second image or series of images to the first image or series of images respectively. The processor may be programmed to stabilize the second image in relation to the first image and to limit drift. The processor may also be programmed to monitor the first and second images for cardiovascular periodicity, image quality, temporal change and vasomotion. It can also match the first series of images and the second series of images.

68 Claims, 15 Drawing Sheets

U.S. PATENT DOCUMENTS

| | | |
|---|---|---|
| 5,538,004 | 7/1996 | Bamber ............................... 128/916 X |
| 5,566,674 | 10/1996 | Weng . |
| 5,568,811 | 10/1996 | Olstad . |
| 5,575,286 | 11/1996 | Weng et al. . |
| 5,582,178 | 12/1996 | Yock . |
| 5,601,085 | 2/1997 | Ostensen et al. . |
| 5,608,849 | 3/1997 | King, Jr. . |
| 5,623,929 | 4/1997 | Weng . |
| 5,655,535 | 8/1997 | Friemel et al. . |
| 5,676,151 | 10/1997 | Yock . |
| 5,683,451 | 11/1997 | Lenker et al. . |
| 5,724,977 | 3/1998 | Yock et al. . |
| 5,724,978 | 3/1998 | Tenhoff . |
| 5,752,522 | 5/1998 | Murphy . |
| 5,771,895 | 6/1998 | Slager . |
| 5,830,145 | 11/1998 | Tenhoff ............................... 600/467 X |
| 5,865,178 | 2/1999 | Yock . |
| 5,876,345 | 3/1999 | Eaton et al. ......................... 600/466 X |
| 5,879,305 | 3/1999 | Yock et al. . |
| 5,885,218 | 3/1999 | Teo et al. ................................ 600/443 |
| 5,899,861 | 5/1999 | Freimel et al. ......................... 600/443 |
| 5,902,245 | 5/1999 | Yock . |
| 5,921,934 | 7/1999 | Teo ......................................... 600/466 |
| 5,971,895 | 6/1998 | Slager ................................ 600/467 X |

OTHER PUBLICATIONS

W. Li et al., "Temporal Correlation of Blood Scattering Signals In Vivo from Radiofrequency Intravascula Ultrasound", Ultrasound in Medicine & Biology, vol. 22, No. 5, 1996, pp. 583–590.

M. de Kroon et al., "Cyclic Changes of Blood Echogenicity In High–Frequency Ultrasound", Ultrasound in Medicine & Biology, vol. 17, No. 7, 1991, pp. 723–728.

W. Li et al., "Temporal Averaging For Quantification of Lumen Dimensions in Intravascular Ultrasound Images", Ultrasound in Medicine & Biology, vol. 20, No. 2, 1994, pp. 117–122.

G. Pasterkamp et al., "Intravascular Ultrasound Image Subtraction: A Contrast Enhancing Technique To Facilitate Automatic Three–Dimensional Visualization of The Arterial Lumen", Ultrasound in Medicine & Biology, vol. 21, No. 7 1995, pp. 913–918.

G. Pasterkamp et al., "Discrimination of Intravascular Lumen and Dissections In Single Intravascular Ultrasound Images Using Subtraction, Conventional Averaging and Saline Flush", Ultrasound in Medicine & Biology, vol. 21, No. 2, 1995, pp. 149–156.

M. Post et al., "Computation Of A Location Shift Between Two Subsequent Intravascular Ultrasound Registrations By Cross–Correlation Analysis Of The Lumen Area Functions", Ultrasound in Medicine & Biology, vol. 22, No. 2, 1996, pp. 239–243.

N. Bruining et al., "Dynamic Three–dimensional Reconstruction of ICUS Images Based on an ECG–Gated Pull–Back Device", IEEE Computers in Cardiology, 1995, pp. 633–636.

N. Bruining et al., "Dynamic Three–dimensional Reconstruction of Implanted Intracoronary Stent Structures Using ICUS Images", the Thoraxcentre Journal, vol. 8, No. 4, Dec. 1996, pp. 18–24.

P. Dhawale et al., "Calibrated 3–D Reconstruction of Intracoronary Ultrasound Images with Cardiac Gating and Catheter Motion Compensation", IEEE Computers in Cardiology, 1992, pp. 31–34.

M. Van Horn et al., "Intracoronary Ultrasound Catheter Motion Compensation Using the Generalized Hough Transform", IEEE Computers in Cardiology, 1994, pp. 293–296.

J.G. Bosch et al., "Automatic Frame–to–Frame Contour Detection in Echocardiograms Using Motion Estimation", IEEE Computers in Cardiology, 1992, pp. 351–354.

L. Wenguang et al., "Semiautomatic Frame–to–Frame Tracking of the Luminal Border from Intravascular Ultrasound", IEEE Computers in Cardiology, 1992, pp. 353–356.

G. Pasterkamp et al., "Discrimination of the Intravascular Lumen and Dissections in a Single 30–MHz US Image: Use of 'Confounding' Blood Backscatter to Advantage", Radiology, vol. 187, No. 3, 1993, pp. 871–872.

A. Skovoroda et al., "Theoretical Analysis and Verfication of Ultrasound Displacement and Strain Imaging", IEEE Transactions on Ultrasonics, Ferroelectrics, and Frequency Control, vol. 41, No. 3, May 1994, pp. 302–313.

B. Shapo et al., "Displacement and Strain Imaging of Coronary Arteries with Intraluminal Ultrasound", IEEE Transactions on Ultrasonics, Ferroelectrics, and Frequency Control, vol. 43, No. 2, Mar. 1996, pp. 234–246.

C. von Birgelen et al., "Morphometric Analysis in Three–dimensional Intracoronary Ultrasound: An In Vitro and In Vivo Study Performed With a Novel System for the Contour Detection of Lumen and Plaque", American Heart Journal, vol. 132, No. 3, 1996, pp. 516–527.

W. Li et al., "Semi–Automatic Contour Detection for Volumetric Quantification of Intracoronary Ultrasound", IEEE Computers in Cardiology, 1994, pp. 277–280.

D. Herrington et al., "Semi–Automated Boundary Detection for Intravascular Ultrasound", IEEE Computers in Cardiology, 1992, pp. 103–106.

M. Sonka et al., "Automated Segmentation of Coronary Wall and Plaque from Intravascular Ultrasound Image Sequences", IEEE Computers in Cardiology, 1994, pp. 281–284.

M. Van Horn et al., "3–D Intracoronary Ultrasound Surface Detection Using the 'Thin–Plate' Model", IEEE Computers in Cardiology, 1996, pp. 49–52.

Marraccini et al., Quantitative Analysis Of Coronary Dynamics By Time–Dependent Ultrasound Imaging, Apr. 1, 1995, Journal of Electronic Imaging, vol. 4, No. 2, pp. 123–130.

Laban et al. "Angus: A New Approach to Three–Dimensional Reconstruction of Coronary Vessels by Combined Use of Angiography and Intravascular Ultrasound", Sep. 10, 1995, Computers In Cardiology 1995, pp. 325–328.

a.

b.

Original image                Image with Drift

Non stabilized image          Stabilized image a. Baseline Vessel

Cartesian representation

Polar representation b. Global contraction

Cartesian representation

Polar representation c. Global dilation

Cartesian representation

Polar representation a. Baseline b. Local vasomotion

| # IMAGE | 1 | 2 | 3 | 4 | 5 | 6 | 7 | 8 | 9 | 10 |
|---|---|---|---|---|---|---|---|---|---|---|
| CLOSENESS VALUE | 0.8 | 0.83 | 0.89 | 0.85 | 0.82 | 0.87 | 0.9 | 0.88 | 0.86 | 0.84 |
| INTERNAL CROSS-CORRELATION | 1 | 0.9988 | 0.9978 | 0.9993 | 0.9999 | 0.9991 | 0.9982 | | | |

FIG. 10

Original image · Filtered image

Figure 15

| First Film | Reference segment | Corresponding Images from First Film |
|---|---|---|
| #1 | #1 | #5 |
| #2 | #2 | #6 |
| #3 | #3 | #7 |
| #4 | #4 | #8 |
| #5 | #5 | #9 |
| #6 | #6 | #10 |
| #7 | #7 | #11 |
| #8 | #8 | #12 |
| #9 | #9 | #13 |
| #10 | #10 | #14 |
| #11 | | |
| #12 | | |
| #13 | | |
| #14 | | |
| #15 | | |
| #16 | | |
| #17 | | |
| #18 | | |
| #19 | | |
| #20 | | |
| #... | | |

INTRAVASCULAR ULTRASOUND ENHANCED IMAGE AND SIGNAL PROCESSING

This application is a division of prior application Ser. No. 08/879,125, filed Jun. 19, 1997.

FIELD OF THE INVENTION

The present invention relates to a device and method for enhanced image and signal processing for Intravascular Ultrasound ("IVUS"), and more specifically, to a device and method for processing IVUS image and signal information which will enhance the quality and utility of IVUS images.

BACKGROUND INFORMATION

IVUS images are derived from a beam of ultrasonic energy projected by apparatus such as a transducer or transducer array located around, along or at the tip of a catheter inserted within a blood vessel. An ultrasound beam from the apparatus is continuously rotated within the blood vessel forming a 360° internal cross sectional image, i.e., the image is formed in a transverse (X-Y) plane. Depending on the specific apparatus configuration, the image may be derived either from the same transverse plane of the apparatus or from a transverse plane found slightly forward (i.e., distal) of the transverse plane of the apparatus. If the catheter is moved inside and along the blood vessel (i.e., along the Z-axis), images of various segments (series of consecutive cross sections) of the vessel may be formed and displayed.

IVUS may be used in all types of blood vessels, including but not limited to arteries, veins and other peripheral vessels, and in all parts of a body.

The ultrasonic signal that is received (detected) is originally an analog signal. This signal is processed using analog and digital methods so as to eventually form a set of vectors comprising digitized data. Each vector represents the ultrasonic response of a different angular sector of the vessel, i.e., a section of the blood vessel. The number of data elements in each vector (axial sampling resolution) and the number of vectors used to scan a complete cross section (lateral sampling resolution) of the vessel may vary depending on the type of system used.

The digitized vectors may initially be placed into a two-dimensional array or matrix having Polar coordinates, i.e., $A(r, \theta)$. In this Polar matrix, for example, the X axis corresponds to the r coordinate and the Y axis corresponds to the $\theta$ coordinate. Each value of the matrix is a value (ranging from 0–255 if the system is 8 bit) representing the strength of the ultrasonic response at that location.

This Polar matrix is not usually transferred to a display because the resultant image will not be easily interpreted by a physician. The information stored in the Polar matrix $A(r, \theta)$ usually undergoes several processing stages and is interpolated into Cartesian coordinates, e.g., X and Y coordinates $(A(X, Y))$ that are more easily interpreted by a physician. Thus, the X and Y axis of matrix $A(X, Y)$ will correspond to the Cartesian representation of the vessel's cross-section. The information in the Cartesian matrix possibly undergoes further processing and is eventually displayed for analysis by a physician. Images are acquired and displayed in a variable rate, depending on the system. Some systems can acquire and display images in video-display rate, e.g., up to about 30 images per second.

IVUS examination of a segment of a bodily lumen, i.e., vessel is generally performed by situating the catheter distal (i.e., downstream) to the segment to be reviewed and then the catheter is pulled back (pullback) slowly along the bodily lumen (Z-axis) so that successive images that form the segment are continuously displayed. In many cases the catheter is connected to a mechanical pulling device which pulls the catheter at a constant speed (i.e., a typical speed is approximately 0.5–1 mm/sec.).

In IVUS imaging systems today the technique described above for displaying an image of a cross section of a bodily lumen, e.g., blood vessel, is generally used. These systems are deficient, however, because they do not include any form of stabilization of the images to compensate for movements of the catheter and/or bodily lumen, e.g., blood vessel. It is well known that during IVUS imaging of a bodily lumen, there is always motion exhibited by the catheter and/or the bodily lumen. This motion might be exhibited in the transverse (X-Y) plane, along the vessel axis (Z axis) or a combination of those movements. The imaging catheter can also be tilted in relation to the vessel so that the imaging plane is not perpendicular to the Z axis (This movement shall be termed as angulation). These movements are caused by, among other things, beating of the heart, blood and/or other fluid flow through the lumen, vasomotion, forces applied by the physician, and other forces caused by the physiology of the patient.

In IVUS systems today, when the imaging catheter is stationary or when performing slow manual or mechanical pullback, relative movement between the catheter and the lumen is the primary factor for the change in appearance between successive images, i.e., as seen on the display and/or on film or video. This change in appearance occurs because the rate of change of an image due to movements is much greater than the rate of change in the real morphology due to pullback.

Stabilization occurs when the images include compensation for the relative movement between the catheter and the lumen in successive images. Because none of the IVUS systems used today perform stabilization, there is no compensation for or correction of relative movements between the catheter and the lumen. As a result, morphological features are constantly moving or rotating, i.e., on the display and/or film or video. This makes it difficult for the physician to accurately interpret morphology in an IVUS dynamic display. Furthermore, when non-stabilized IVUS images are fed as an input to a processing algorithm such as 3D reconstruction or different types of filter that process a set of successive images, this can lead to degraded performance and misdiagnosis or inaccurate determinations.

Current IVUS imaging apparatus or catheters may have occasional malfunctions of an electronic or mechanical origin. This can cause displayed images to exhibit both recognized or unrecognized artifacts and obscure the real morphology. Currently there is no automatic methods to determine whether images posses these types of artifacts which hamper the analysis of the images of the vessel or bodily lumen.

The behavior of cardiovascular function is generally periodic. The detection of this periodicity and the ability to establish correlation between an image and the temporal phase in the cardiac cycle to which it belongs is referred to as cardiac gating.

Currently, cardiac gating is performed by using an external signal, usually an ECG (Electro-Cardiogram). However, ECG gating requires both the acquisition of the ECG signal and its interleaving (or synchronization) with the IVUS image. This requires additional hardware/software.

Morphological features in IVUS images of blood vessels can be broken into three general categories: the lumen, i.e., the area through which the blood or other bodily fluid flows; the vessel layers; and the exterior, i.e., the tissue or morphology outside of the vessel. Blood in most IVUS films (images) is characterized by a rapidly changing speckular pattern. The exterior of the vessel also alternates with high temporal frequency. Currently, the temporal behavior of pixels and their textural attributes are not monitored automatically.

Vasomotion in the context of bodily lumens, e.g., blood vessel, is defined as the change in the caliber of the lumen, e.g., vessel. This change can be brought about by natural circumstances or under induced conditions. Vasomotion can have a dynamic component, i.e., dynamic change of the lumen's dimensions, e.g., vessel's caliber (contraction and dilation) during the cardiovascular cycle, and a baseline static component, i.e., a change in the baseline caliber of the lumen, e.g., vessel.

Vasomotion can be expressed as quantitative physiological parameters indicating the ability of the lumen, e.g., vessel to change its caliber under certain conditions. These types of parameters have current and possibly future medical and diagnostic importance in providing information regarding the state of the lumen, e.g., vessel and the effect of the therapy performed.

IVUS can be used to monitor vasomotion because it provides an image of the lumen's baseline caliber and its dynamic changes. Additionally, IVUS can be used to monitor whether the vasomotion is global (uniform), i.e., where the entire cross-section of the lumen contracts/dilates in the same magnitude and direction. IVUS can also be used to determine whether the vasomotion is non-uniform which leads to local changes in the caliber of the lumen, i.e., different parts of the lumen cross-section behave differently.

Currently, all types of vasomotion monitoring by IVUS are performed manually. This is tedious, time consuming, and prevents monitoring of the vasomotion in real time.

Interpretation of IVUS images is achieved through analysis of the composition of the static images and monitoring their temporal behavior. Most IVUS images can be divided into three basic parts. The most inner section is the flow passage of the lumen, i.e., the cavity through which matter, i.e., blood, flows. Around the flow passage is the actual vessel, which may include blood vessels and any other bodily vessels, which is composed of multiple layers of tissue (and plaque, if diseased). Outside the vessel other tissue which may belong to the surrounding morphology, for example, the heart in a coronary vessel image.

When the IVUS film is viewed dynamically, i.e., in film format, the pixels corresponding to matter flowing through the vessel and to the morphology exterior to the vessel exhibit a different temporal behavior than the vessel itself. For example, in most IVUS films, blood flowing through the vessel is characterized by a frequently alternating speckular pattern. The morphology exterior to the vessel also exhibits frequent alternation. Currently the temporal behavior of pixels in dynamic IVUS images is not monitored automatically.

In current IVUS displays, if designed into the system, high frequency temporal changes are suppressed by means such as averaging over a number of images. However, this sometimes fails to suppress the appearance of features with high amplitudes, i.e., bright gray values, and it also has a blurring effect.

The size of the flow passage of the lumen is a very important diagnostic parameter. When required for diagnosis, it is manually determined by, for example, a physician. This is accomplished by drawing the contour of the flow passage borders superimposed on a static image, e.g., frozen on video or on a machine display. This method of manual extraction is time consuming, inaccurate and subject to bias.

Currently, there is commercial image processing software for the automatic extraction of the flow passage. However, these are based on the gray value composition of static images and do not take into account the different temporal behavior exhibited by the material, e.g., blood flowing through the passage as opposed to the vessel layers.

During treatment of vessels, it is common practice to repeat IVUS pullback examinations in the same vessel segments. For example, a typical situation is first to review the segment in question, evaluate the disease (if any), remove the IVUS catheter, consider therapy options, perform therapy, e.g., PTCA-"balloon" or stenting, and then immediately thereafter reexamine the treated segment using IVUS in order to assess the results of the therapy. To properly evaluate the results and fully appreciate the effect of the therapy performed, it is desirable that the images of the pre-treated and post-treated segments, which reflect cross sections of the vessel lying at the same locations along the vessel's Z-axis (i.e., corresponding segments), be compared. To accomplish this comparison it must be determined which locations in the films of the pre-treatment IVUS images and post-treatment IVUS images correspond to one another. This procedure, called matching (registration) allows an accurate comparison of pre- and post-treatment IVUS images.

Currently, matching is usually performed by viewing the IVUS pullback films of pre- and post-treatment segments, one after the other or side by side by using identifiable anatomical landmarks to locate the sequences that correspond visually to one another. This method is extremely imprecise and difficult to achieve considering that the images are unstable and often rotate and/or move around on the display due to the absence of stabilization and because many of the anatomical landmarks found in the IVUS pullback film of the pre-treatment segment may be disturbed or changed as a result of the therapy performed on the vessel. Furthermore, the orientation and appearance of the vessel is likely to change as a result of a different orientations and relative positions of the IVUS catheter in relation to the vessel due to its removal and reinsertion after therapy is completed. The matching that is performed is manual and relies primarily on manual visual identification which can be extremely time consuming and inaccurate.

SUMMARY OF THE INVENTION

The present invention solves the problems associated with IVUS imaging systems currently on the market and with the prior art by providing physicians with accurate IVUS images and image sequences of the morphology being assessed, thereby enabling more accurate diagnosis and evaluation.

The present invention processes IVUS image and signal information to remove distortions and inaccuracies caused by various types of motion in both the catheter and the bodily lumen. This results in both enhanced quality and utility of the IVUS images. An advantage provided by the present invention is that individual IVUS images are stabilized with respect to prior image(s), thereby removing negative effects on any later processing of multiple images. If the movements in each image are of the transverse type, then it is possible for the motion to be completely compensated for in each acquired image.

The present invention also allows volume reconstruction algorithms to accurately reproduce the morphology since movement of the bodily lumen is stabilized. The present invention is applicable to and useful in any type of system where there is a need to stabilize images (IVUS or other) because a probe (e.g., ultrasonic or other) moving through a lumen experiences relative motion (i.e., of the probe and/or of the lumen).

The present invention provides for detection of an ultrasonic signal emitted by ultrasonic apparatus in a bodily lumen, conversion of the received analog signal into Polar coordinates (A(r, θ)), stabilization in the Polar field, converting the stabilized Polar coordinates into Cartesian coordinates (A(X, Y)), stabilization in the Cartesian field and then transferring the stabilized image as Cartesian coordinates to a display. Stabilized images, either in Polar or Cartesian coordinates, may be further processed prior to display or they might not be displayed. Conversion into Cartesian coordinates and/or stabilization in the Cartesian field may be done at any point either before or after stabilization in the Polar field. Additionally, either of Polar or Cartesian stabilization may be omitted, depending on the detected shift in the image and/or other factors. Furthermore, additional forms of stabilization may be included or omitted depending on the detected shift and/or other factors.

For example, stabilization of rigid motion may be introduced to compensate for rotational motion (angular) or global vasomotion (expansion or contraction in the r direction) in the Polar field and/or for Cartesian displacement (X and/or Y direction) in the Cartesian field.

Transverse rigid motion between the representations of successive images is called a "shift," i.e., a uniform motion of all morphological features in the plane of the image. To stabilize IVUS images, the first step that is performed is "shift evaluation and detection." This is where the shift (if any) between each pair of successive images is evaluated and detected. The system may utilize a processor to perform an operation on a pair of successive IVUS images to determine whether there has been a shift between such images. The processor may utilize a single algorithm or may select from a number of algorithms to be used in making this determination.

The system utilizes the algorithm(s) to simulate a shift in an image and then compares this shifted image to its predecessor image. The comparisons between images are known as closeness operations which may also be known in the prior art as matching. The system performs a single closeness operation for each shift. The results of the series of closeness operations is evaluated to determine the location (direction and magnitude) of the shifted image that bears the closest resemblance to the predecessor unshifted image. An image can of course be compared in the same manner to its successor image. After the actual shift is determined, the current image becomes the predecessor image, the next image becomes the current image and the above operation is repeated.

Using shift evaluation and detection, the system determines the type of transverse shift, e.g., rotational, expansion, contraction, displacement (Cartesian), etc., along with the direction and magnitude of the shift. The next step is "shift implementation." This is where the system performs an operation or a series of operations on successive IVUS images to stabilize each of the images with respect to its adjacent predecessor image. This stabilization utilizes one or multiple "reverse shifts" which are aimed at canceling the detected shift. The system may include an algorithm or may select from a number of algorithms to be used to implement each "reverse shift." The logic which decides upon what reverse shift will actually be implemented on an image, prior to its feeding to further processing or display, is referred to as "shift logic". Once the IVUS images are stabilized for the desired types of detected motion, the system may then transfer the Cartesian (or Polar) image information for further processing and finally for display where the results of stabilization may be viewed, for example, by a physician. Alternatively, stabilization can be invisible to the user in the sense that stabilization can be used prior to some other processing steps, after which, resulted images are projected to the display in their original non-stabilized posture or orientation.

It is possible that the transverse motion between images will not be rigid but rather of a local nature, i.e., different portions of the image will exhibit motion in different directions and magnitudes. In that case the stabilization methods described above or other types of methods can be implemented on a local basis to compensate for such motion.

The present invention provides for detection of the cardiac periodicity by using the information derived only from IVUS images without the need for an external signal such as the ECG. This process involves closeness operations which are also partly used in the stabilization process. One important function of detecting periodicity (i.e., cardiac gating), when the catheter is stationary or when performing controlled IVUS pullback, is that it allows the selection of images belonging to the same phase in successive cardiac cycles. Selecting images based on the cardiac gating will allow stabilization of all types of periodic motion (including transverse, Z-axis and angulations) in the sense that images are selected from the same phase in successive heart-beats. These IVUS images, for example, can be displayed and any gaps created between them may be compensated for by filling in and displaying interpolated images. The IVUS images selected by this operation can also be sent onward for further processing.

The closeness operations used for periodicity detection can also be utilized for monitoring image quality and indicate artifacts associated with malfunction of the imaging and processing apparatus.

Operations used for shift evaluation can automatically indicate vasomotion. This can serve the stabilization process as vasomotion causes successive images to differ because of change in the vessel's caliber. If images are stabilized for vasomotion, then this change is compensated for. Alternatively, the information regarding the change in caliber may be displayed since it might have physiological significance. Monitoring of vasomotion is accomplished by applying closeness operations to successive images using their Polar representations, i.e., A(r, θ). These operations can be applied between whole images or between corresponding individual Polar vectors (from successive images), depending on the type of information desired. Since global vasomotion is expressed as a uniform change in the lumen's caliber it can be assessed by a closeness operation which takes into account the whole Polar image. In general, any operation suitable for global stabilization in the Polar representation can be used to assess global vasomotion.

Under certain conditions during IVUS imaging there may be non-uniform vasomotion, i.e., movement only in certain sections of the IVUS image corresponding to specific locations in the bodily lumen. This may occur, for example, where an artery has a buildup of plaque in a certain location, thereby allowing expansion or contraction of the artery only in areas free of the plaque buildup. When such movement is detected the system is able to divide the ultrasound signals representing cross sections of the bodily lumen into multiple segments which are then each processed individually with respect to a corresponding segment in the adjacent image using certain algorithm(s). The resulting IVUS images may then be displayed. This form of stabilization may be used individually or in conjunction with the previously discussed stabilization techniques. Alternatively, the information regarding the local change in vessel caliber can be displayed since it might have physiological significance.

The temporal behavior of pixels and their textural attributes could serve for: enhancement of display; and automatic segmentation (lumen extraction). If monitored in a stabilized image environment then the performance of the display enhancement and segmentation processes may be improved.

According to the present invention, the temporal behavior of IVUS images may be automatically monitored. The information extracted by such monitoring can be used to improve the accuracy of IVUS image interpretation. By filtering and suppressing the fast changing features such as the matter, e.g., blood flowing through the vessel and the morphology exterior to the vessel as a result of their temporal behavior, human perception of the vessel on both static images and dynamic images, e.g., images played in cine form, may be enhanced.

Automatic segmentation, i.e., identification of the vessel and the matter, e.g., blood flowing through the vessel may be performed by using an algorithm which automatically identifies the matter, e.g., blood based on the temporal behavior of textural attributes formed by its comprising pixels. The temporal behavior that is extracted from the images can be used for several purposes. For example, temporal filtering may be performed for image enhancement, and detection of the changes in pixel texture may be used for automatic identification of the lumen and its circumference.

In all IVUS images, the catheter itself (and imaging apparatus) is best to be eliminated from the image prior to performing stabilization or for monitoring. Failure to eliminate the catheter might impair stabilization techniques and monitoring. Elimination of the catheter may be performed automatically since its dimensions are known.

The present invention also provides for automatic identification (i.e., matching or registration) of corresponding frames of two different IVUS pullback films of the same segment of a vessel, e.g., pre-treatment and post-treatment. To compare a first IVUS pullback film, i.e., a first IVUS imaging sequence, with a second IVUS pullback film, i.e., a second IVUS imaging sequence, of the same segment of a bodily lumen, for example, captured on video, film or in digitized form, the imaging sequences must be synchronized. Matching, which will achieve this synchronization, involves performing closeness operations between groups of consecutive images belonging to the two sets of IVUS imaging sequences.

Out of one imaging sequence a group of consecutive images, termed the reference group, is selected. This group should be selected from a portion of the vessel displayed in both imaging sequences and it should be a portion on which therapy will not be performed since the morphology of the vessel is likely to change due to therapy. Another condition for this matching process is that the two imaging sequences are acquired at a known, constant and preferably the same pullback rate.

Closeness operations are performed between the images of the reference group and the images from the second group which has the same number of successive images extracted from the second imaging sequence. This second group of images is then shifted by a single frame with respect to the reference group and the closeness operations are repeated. This may be repeated for a predetermined number of times and the closeness results of each frame shift are compared to determine maximal closeness. Maximal closeness will determine the frame displacement between the images of the two imaging sequences. This displacement can be reversed in the first or second film so that corresponding images may be automatically identified and/or viewed simultaneously.

Thus, corresponding images may be viewed, for example, to determine the effectiveness of any therapy performed or a change in the morphology over time.

Additionally, the various types of stabilization discussed above may be implemented within or between the images in the two sequences, either before, during or after this matching operation. Thus, the two films can be displayed not only in a synchronized fashion, but also in the same orientation and posture with respect to one another.

BRIEF DESCRIPTION OF THE DRAWINGS

FIG. 10 shows a table of a group of cross-correlation coefficient values (middle row) belonging to successive images (numbers 1 through 10 shown in the top row) and the results of internal cross-correlations (bottom row).

FIG. 15 illustrates the time sequence of a first film (left column), reference segment from the second film (middle column) and the images from the first film which correspond (or match) the images of the reference segment (right column).

DETAILED DESCRIPTION

In intravascular ultrasound (IVUS) imaging systems the ultrasonic signals are emitted and received by the ultrasonic apparatus, for example, a transducer or transducer array, processed and eventually arranged as vectors comprising digitized data. Each vector represents the ultrasonic response of a different angular sector of the bodily lumen. The number of data elements in each vector (axial sampling resolution) and the number of vectors used to scan the complete cross-section (lateral sampling resolution) of the bodily lumen depends on the specific IVUS system used.

Figure 1:
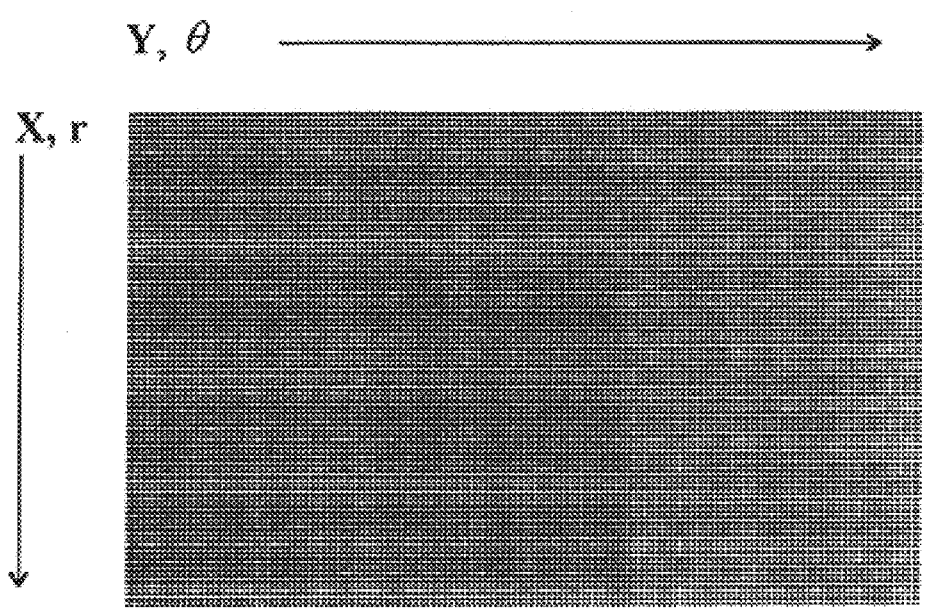
FIGS. 1(a) and (b) show a two-dimensional array or matrix of an image arranged in digitized vectors in Polar and Cartesian coordinates, respectively.
Figure 1:
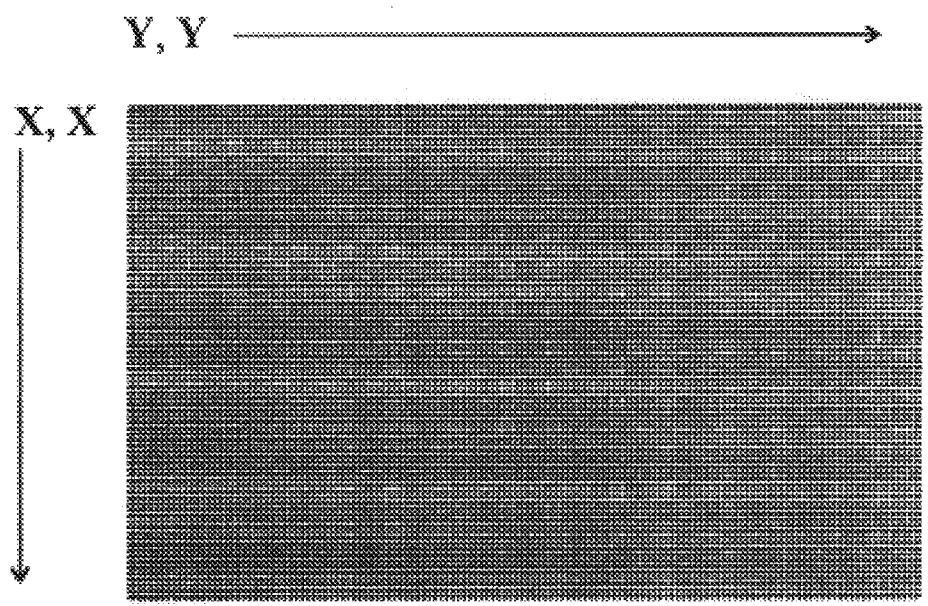

The digitized vectors are initially packed into a two-dimensional array or matrix which is illustrated in FIG. 1(a). Generally, this matrix has what are known as Polar coordinates, i.e., coordinates A(r, θ). The X-axis of the matrix shown in FIG. 1(a) corresponds to the r coordinate while the Y-axis of the matrix corresponds to the θ coordinate. Each value of the matrix is generally a gray value, for example, ranging from 0–255 if it is 8 bit, representing the strength of the ultrasonic signal at that corresponding location in the bodily lumen. This Polar matrix may then be converted into a Cartesian matrix as shown in FIG. 1(b) having an X-axis and Y-axis which correspond to the Cartesian representation of the vessel's cross-section. This image may then be further processed and transferred to a display. The initial array and the display may each utilize either Polar or Cartesian coordinates. The values for the matrix may be other than gray values, for example, they may be color values or other values and may be less than or more than 8 bits.

During an IVUS imaging pullback procedure the bodily lumen, hereinafter referred to as a vessel, and/or the imaging catheter may experience several modes of relative motion. These types of motion include: (1) Rotation in the plane of the image, i.e., a shift in the θ-coordinate of the Polar image; (2) Cartesian displacement, i.e., a shift in the X and/or Y coordinate in the Cartesian image; (3) Global vasomotion, characterized by a radial contraction and expansion of the entire vessel, i.e., a uniform shift in the r-coordinate of the Polar image; (4) Local vasomotion, characterized by a radial contraction and expansion of different parts of the vessel with different magnitudes and directions, i.e., local shifts in the r-coordinate of the Polar image; (5) Local motion, characterized by different tissue motion which vary depending on the exact location within the image; and (6) Through plane motion, i.e., movements which are perpendicular or near perpendicular (angulation) to the plane of the image.

Stabilization of successive raw images is applicable to the first 5 types of motion described above because motion is confined to the transverse plane. These types of motion can be compensated for, and stabilization achieved, by transforming each current image so that its resemblance to its predecessor image is maximized. The first 3 types of motion can be stabilized using closeness operations which compare whole or large parts of the images one to another. This is because the motion is global or rigid in its nature. The 4th and 5th types of motion are stabilized by applying closeness operations on a localized basis because different parts of the image exhibit different motion. The 6th type of motion can be only partly stabilized by applying closeness operations on a localized basis. This is because the motion is not confined to the transverse plane. This type of motion can be stabilized using cardiovascular periodicity detection.

The next sections shall describe methods for global stabilization, followed by a description of methods for local stabilization. Stabilization using cardiovascular periodicity detection shall be described in the sections discussing periodicity detection.

To achieve global stabilization, shift evaluation is performed using some type of closeness operation. The closeness operation measures the similarity between two images. Shift evaluation is accomplished by transforming a first image and measuring its closeness, i.e., similarity, to its predecessor second image. The transformation may be accomplished, for example, by shifting the entire first image along an axis or a combination of axes (X and/or Y in Cartesian coordinates or r and/or θ in Polar coordinates) by a single pixel (or more). Once the transformation, i.e., shift is completed the transformed first image is compared to the predecessor second image using a predefined function. This transformation is repeated, each time by shifting the first image an additional pixel (or more) along the same and/or other axis and comparing the transformed first image to the predecessor second image using a predefined function. After all of the shifts are evaluated, the location of the global extremum of the comparisons using the predefined function will indicate the direction and magnitude of the movement between the first image and its predecessor second image.

Figure 2:
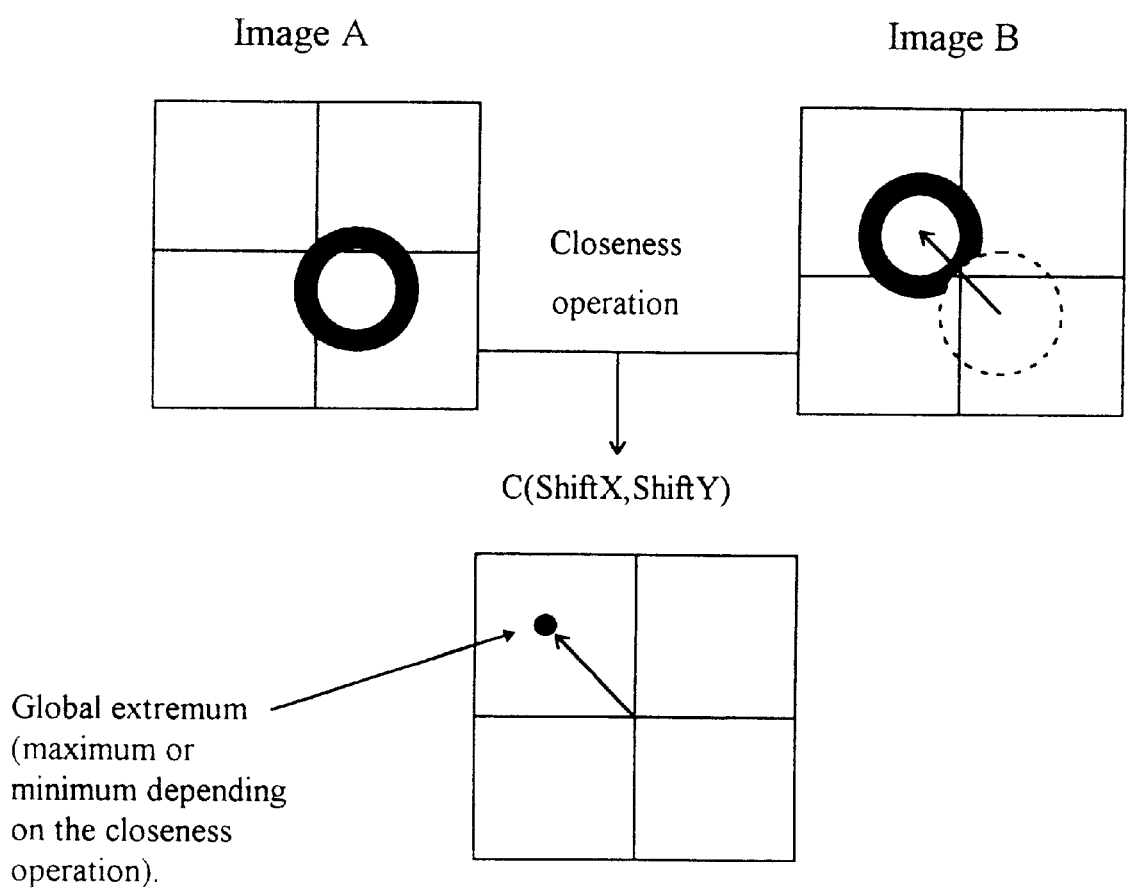
FIG. 2 illustrates the results of a shift evaluation between two successive images in Cartesian coordinates.

For example, FIG. 2 illustrates the results of a shift evaluation between two successive images in Cartesian coordinates. Image A is a predecessor image showing a pattern, e.g., a cross-section of a vessel, whose center is situated in the bottom right quadrant of the matrix. Image B is a current image showing the same pattern but moved in an upward and left direction and situated in the upper left quadrant of the matrix. The magnitude and direction of the movement of the vessel's center is indicated by the arrow. The bottom matrix is the C(shiftX, shiftY) matrix which is the resulting matrix after performing shift evaluations using some type of closeness operation.

There are many different algorithms or mathematical functions that can be used to perform the closeness operations. One of these is cross-correlation, possibly using Fourier transform. This is where the current and predecessor images each consisting of, for example, 256×256 pixels, are each Fourier transformed using the FFT algorithm. The conjugate of the FFT of the current image is multiplied with the FFT of the predecessor image. The result is inversely Fourier transformed using the IFFT algorithm. The formula for cross-correlation using Fourier transform can be shown as follows:

$$C = \text{real}(ifft2((fft2(A))^* \text{conj}(fft2(B))))$$

where:
A=predecessor image matrix (e.g., 256×256);
B=current image matrix (e.g., 256×256);
fft2=two dimensional FFT;
ifft2=two dimensional inverse FFT;
conj=conjugate;
real=the real part of the complex expression;
*=multiplication of element by element; and
C=cross-correlation matrix.

Evaluating closeness using cross-correlation implemented by Fourier transform is actually an approximation. This is because the mathematical formula for the Fourier transform relates to infinite or periodic functions or matrices, while in real life the matrices (or images) are of a finite size and not necessarily periodic. When implementing cross-correlation using FFT, the method assumes periodicity in both axes.

As a result, this formula is a good approximation and it reflects the actual situation in the θ-axis of the Polar representation of the image, however, it does not reflect the actual situation in the r-axis of the Polar representation or of the X- or Y-axis of the Cartesian representation of the image.

There are a number of advantages to cross-correlation utilizing FFT. First, all values of the cross-correlation matrix C(shiftX, shiftY) are calculated by this basic operation. Furthermore, there is dedicated hardware for the efficient implementation of the FFT operation, i.e. Fourier transform chips or DSP boards.

Another algorithm that can be used to perform closeness operations is direct cross-correlation, either normalized or not. This is achieved by multiplying each pixel in the current shifted image by its corresponding pixel in the predecessor image and summing up all of the results and normalizing in the case of normalized cross-correlation. Each shift results in a sum and the actual shift will be indicated by the largest sum out of the evaluated shifts. The formula for cross-correlation can be shown by the following formula:

$$C(shiftX, shiftY) = \sum_{x,y} B(x - shiftX, y - shiftY) * A(x, y)$$

The formula for normalized cross correlation is $$C(shiftX, shiftY) = \sum_{x,y} B(x - shiftX, y - shiftY) * A(x, y) \bigg/ \sqrt{\sum_{x,y} (B(x - shiftX, y - shiftY) * B(x - shiftX, y - shiftY))} \sqrt{\sum_{x,y} (A(x, y) * A(x, y))}$$

where:

A = predecessor image matrix;

B = current image matrix;

* = multiplication of pixel by corresponding pixel;

$\sum$ = sum of all pixels in matrix;

C = matrix holding results for all performed shifts.

Using this direct method of cross-correlation, C(shiftX, shiftY) can be evaluated for all possible values of shiftX and shiftY. For example, if the original matrices, A and B, have 256×256 pixels each, then shiftX and shiftY values, each ranging from −127 to +128 would have to be evaluated, making a total of 256×256=65,536 shift evaluations in order for C(shiftX, shiftY) to be calculated for all possible values of shiftX and shiftY. Upon completion of these evaluations the global maximum of the matrix is determined.

Direct cross-correlation can be implemented more efficiently by lowering the number of required arithmetic operations. In order to detect the actual shift between images, evaluation of every possible shiftX and shiftY is not necessary. It is sufficient to find the location of the largest C(shiftX, shiftY) of all possible shiftX and shiftY.

A third algorithm that can be used to perform closeness operations is the sum of absolute differences (SAD). This is achieved by subtracting each pixel in one image from its corresponding pixel in the other image, taking their absolute values and summing up all of the results. Each shift will result in a sum and the actual shift will be indicated by the lowest sum. The formula for sum of absolute differences (SAD) can be shown as follows:

$$SAD = absolute(A - B)$$

This formula can also be shown as follows:

$$C(shiftX, shiftY) = \sum_{x,y} \text{abs}(B(x - shiftX, y - shiftY) - A(x, y))$$

where:

A = predecessor image matrix;

B = current image matrix;

abs = absolute value.

− = subtraction of element by element; and $\sum$ = sum of all differences.

While the accuracy of each of these algorithms/formulas may vary slightly depending on the specific type of motion encountered and system settings, it is to be understood that no single formula can, a-priori be classified as providing the best or most accurate results. Additionally, there are numerous variations on the formulas described above and other algorithms/formulas that may be utilized for performing shift evaluation and which may be substituted for the algorithms/formulas described above. These algorithms/formulas also include those operations known in the prior art for use as matching operations.

Referring again to FIG. 2, if the closeness operation performed is cross-correlation, then C(shiftX, shiftY) is called the cross-correlation matrix and its global maximum (indicated by the black dot in the upper left quadrant) will be located at a distance and direction from the center of the matrix (arrow in matrix C) which is the same as that of the center of the vessel in Image B relative to the center of the vessel in image A (arrow in Image B).

If the closeness operation performed is SAD, then the black dot would indicate the global minimum which will be located at a distance and direction from the center of the matrix (arrow in matrix C) which is the same as that of the center of the vessel in Image B relative to the center of the vessel in Image A (arrow in Image B).

Rotational motion is expressed as a shift along the current Polar image in the θ-coordinate relative to its predecessor. The rotational shift in a current image is detected by maximizing the closeness between the current Polar image and its predecessor. Maximum closeness will be obtained when the current image is reversibly shifted by the exact magnitude of the actual shift. In for example, a 256×256 pixel image, the value of the difference (in pixels) between 128 and the θ-coordinate of the maximum in the cross-correlation image (minimum in the SAD image), will indicate the direction (positive or negative) and the magnitude of the rotation.

Global vasomotion is characterized by expansion and contraction of the entire cross section of the vessel. In the Polar image this type of motion is expressed as movement inwards and outwards of the vessel along the r-axis. Vasomotion can be compensated by performing the opposite vasomotion action on a current Polar image in relation to its predecessor Polar image using one of the formulas discussed above or some other formula. In contrast to angular stabilization, vasomotion stabilization does not change the orientation of the image but actually transforms the image by stretching or compressing it.

Cartesian displacement is expressed as a shift in the X-axis and/or Y-axis in the Cartesian image relative to its predecessor. This type of motion is eliminated by shifting the Cartesian image in an opposite direction to the actual shift. Thus, Cartesian displacement, in the Cartesian representation, can be achieved by essentially the same arithmetic operations used for rotational and vasomotion stabilization in the Polar representation.

The number of shift evaluations necessary to locate the global extremum (maximum or minimum, depending on the closeness function) of C(shiftX, shiftY) may be reduced using various computational techniques. One technique, for example, takes advantage of the fact that motion between successive IVUS images is, in general, relatively low in relation to the full dimensions of the Polar and/or Cartesian matrices. This means that C(shiftX, shiftY) can be evaluated only in a relatively small portion around the center of the matrix, i.e., around shiftX=0, shiftY=0. The extremum of that portion is assured to be the global extremum of matrix C(shiftX, shiftY) including for larger values of shiftX and shiftY. The size of the minimal portion which will assure that the extremum detected within it is indeed a global extremum varies depending on the system settings. The number of necessary evaluation operations may be further reduced by relying on the smoothness and monotonous property expected from the C matrix (especially in the neighborhood of the global extremum). Therefore, if the value in the C(shiftX, shiftY) matrix at a certain location is a local extremum (e.g., in a 5×5 pixel neighborhood), then it is probably the global extremum of all of matrix C(shiftX, shiftY).

Implementing this reduction of the number of necessary evaluations can be accomplished by first searching from the center of the matrix (shiftX=0, shiftY=0) and checking a small neighborhood, e.g., 5×5 pixels around the center. If the local extremum is found inside this neighborhood then it is probably the global extremum of the whole matrix C(shiftX, shiftY) and the search may be terminated. If, however, the local extremum is found on the edges of this neighborhood, e.g., shiftX=−2, shiftX=2, shiftY=−2 or shiftY=2, then the search is repeated around this pixel until a C(shiftX, shiftY) value is found that is bigger (smaller) than all of its close neighbors. Because in a large number of images there is no inter-image motion, the number of evaluations needed to locate the global extremum in those cases, will be approximately 5×5=25, instead of the original 65,536 evaluations.

The number of necessary evaluation operations may also be reduced by sampling the images. For example, if 256× 256 sized images are sampled for every second pixel then they are reduced to 128×128 sized matrixes. In this case, direct cross-correlation or SAD, between such matrixes involve 128×128 operations instead of 256×256 operations, each time the images are shifted one in relation to the other. Sampling, as a reduction method for shift evaluation operations can be interleaved with other above described methods for reduction.

Referring again to FIG. 2, as a result of the closeness operation, the indicated shiftX will have a positive value and shiftY a negative value. In order to stabilize Image B, i.e., compensate for the shifts in the X and Y directions, shift logic will reverse the shifts, i.e., change their sign but not their magnitude, and implement these shifts on the matrix corresponding to Image B. This will artificially reverse the shift in Image B and cause Image B to be unshifted with respect to Image A.

The actual values used in the closeness calculations need not necessarily be the original values of the matrix as supplied by the imaging system. For example, improved results may be achieved when the original values are raised to the power of 2, 3 or 4 or processed by some other method.

The imaging catheter and the enclosing sheath appear as constant artifacts in all IVUS images. This feature obscures closeness operations performed between images since it is not part of the morphology of the vessel. It is, therefore, necessary to eliminate the catheter and associated objects from each image prior to performing closeness operations, i.e., its pixels are assigned a value of zero. The elimination of these objects from the image may be performed automatically since the catheter's dimensions are known.

Shift evaluation and implementation may be modular. Thus, shift evaluation and implementation may be limited to either Polar coordinates or Cartesian coordinates individually, or shift evaluation and implementation may be implemented sequentially for Polar and Cartesian coordinates. Presently, because imaging in IVUS systems is generally organized by first utilizing Polar coordinates and then converting into Cartesian coordinates, it is most convenient to perform shift evaluation and implementation in the same sequence. However, the sequence may be modified or changed without any negative effects or results.

The shift evaluation process can be performed along one or two axis. In general, two dimensional shift evaluation is preferred even when motion is directed along one axis. Shift implementation may be limited to both axis, one axis or neither axis.

There is not a necessary identity between the area in the image used for shift evaluation and between the area on which shift implementation is performed. For example, shift evaluation may be performed using a relatively small area in the image while shift implementation will shift the whole image according to the shift indicated by this area.

A trivial shift logic is one in which the shift implemented on each image (thereby forming a stabilized image) has a magnitude equal, and in opposite direction, to the evaluated shift. However, such logic can result in a process defined as Drift. Drift is a process in which implemented shifts accumulate and produce a growing shift whose dimensions are significant in relation to the entire image or display. Drift may be a result of inaccurate shift evaluation or non-transverse inter-image motion at some part of the cardiovascular cycle. When Cartesian stabilization is implemented, drift can cause, for example, the shifting of a relatively large part of the image out of the display. When rotational stabilization is implemented, drift can cause the increasing rotation of the image in a certain direction.

Figure 3:
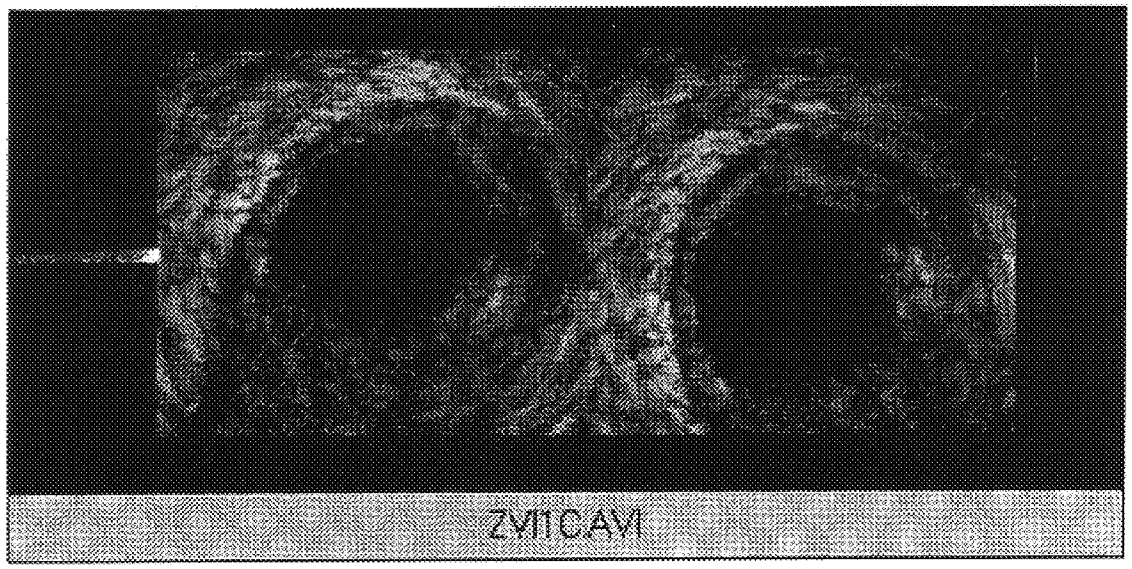
FIG. 3 shows images illustrating the occurrence of drift phenomena in Polar and Cartesian coordinates.

FIG. 3 is an image illustrating the occurrence of drift in Polar and Cartesian coordinates. The left image is the original display of the image while the right image is the same image after Polar and Cartesian stabilization has been performed. Note how the right image is rotated counter-clockwise in a large angle and shifted downward in relation to the left image. In this case, rotational and Cartesian shift implementation do not compensate for actual shifts in the image, but rather arise from inaccurate shift evaluation.

The shift logic must be able to deal with this drift so that there will be a minimal implementation of mistaken evaluated shifts. One method for preventing, or at least limiting drift is by setting a limit to the magnitude of allowable shifts. This will minimize the drift but at the cost of not compensating for some actual shift. Additional methods can be used to prevent or minimize shift. These may possibly be interleaved with cardio-vascular periodicity detection methods discussed later.

Figure 4:
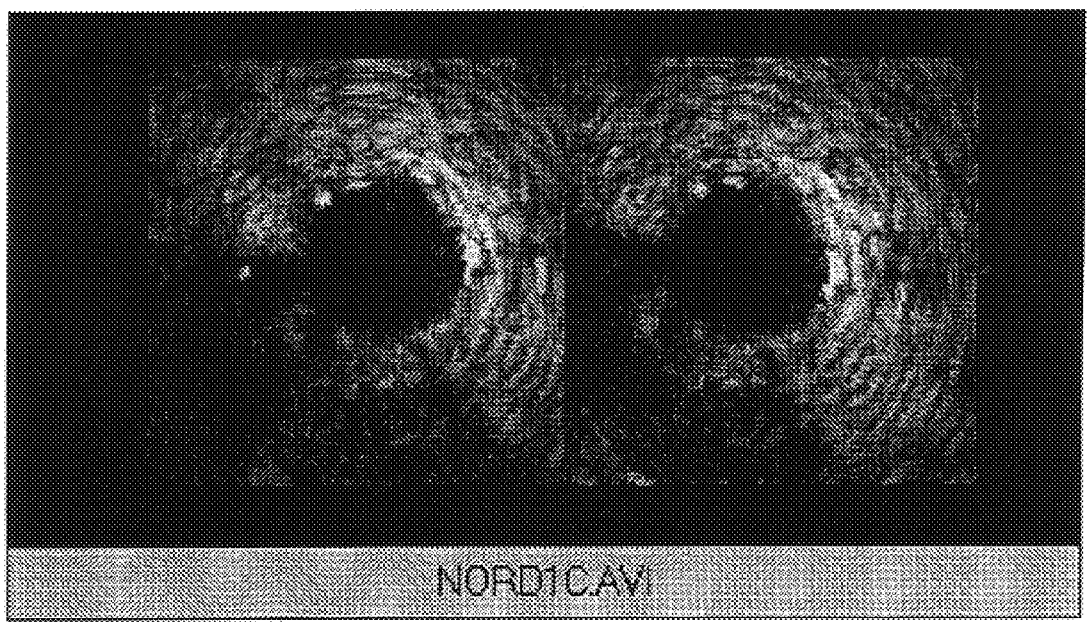
FIG. 4 illustrates the effect of performing stabilization operations (rotational and Cartesian shifts) on an image.

The images shown in FIG. 4 illustrate the effect of performing stabilization operations (rotational and Cartesian shifts) on an image. The left image is an IVUS image from a coronary artery as it would look on a large portion of a regular display (with catheter deleted) while the right image shows how the left image would be displayed after stabilization operations are implemented.

Taking a close look at the left and right images in FIG. 4, certain differences can be observed. First, the right image is slightly rotated in a clockwise direction (i.e., by a few degrees) in relation to the left image. This is the result of rotational stabilization. Next, the right image is translated in a general left direction in relation to the left image. This can be detected by noting the distance of the lumen (cavity) from the edges of the picture in each image. This is a result of Cartesian shift stabilization operations.

The advantages of stabilization of the displayed image cannot be appreciated by viewing single images as shown in FIG. 4. However, viewing a film of such images would readily illustrate the advantages. In a display which does not include stabilization, the location of the catheter would always be situated in the center of the display and the morphological features would move around and rotate on the display. In contrast, in a stabilized display, the location of the catheter would move around while the morphological features would remain basically stationary. Stabilization does not necessarily have to be exhibited on an actual display. It can be invisible to the user in the sense that stabilization will enhance subsequent processing steps, but the actual display will exhibit the resultant processed images in their original (non-stabilized) posture and orientation.

Figure 5:
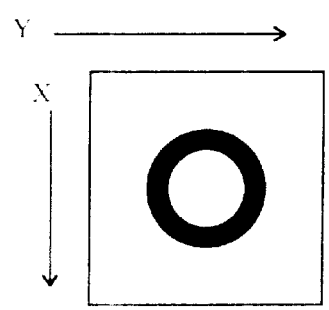
FIG. 5 illustrates global contraction or dilation of a bodily lumen expressed in the Polar representation of the image and in the Cartesian representation of the image.
Figure 5:
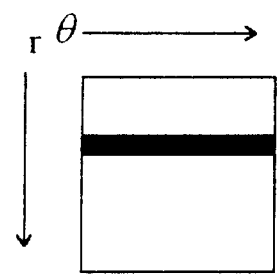
Figure 5:
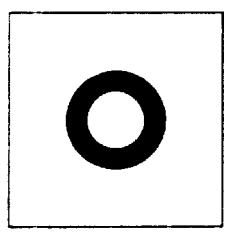
Figure 5:
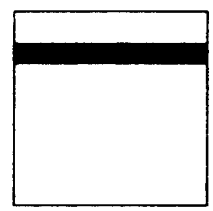
Figure 5:
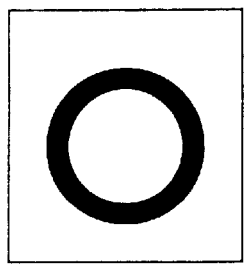
Figure 5:
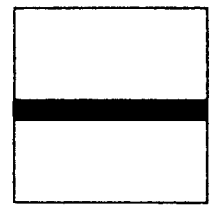

FIG. 5 illustrates global contraction or dilation of a vessel, expressed in the Polar representation of the image as a movement of the features along the r-coordinates, i.e., movement along the Polar vectors. FIG. 5 also shows the same global contraction or dilation expressed in the Cartesian representation of the image. FIG. 5(a) shows the baseline appearance of the cross section of a vessel in both the Polar and Cartesian representations. FIG. 5(b) shows a relative to baseline contraction of the vessel. FIG. 5(c) shows a relative to baseline uniform dilation of the vessel.

Since global vasomotion is expressed as a uniform change in the vessel's caliber, any operation suitable for stabilization in the Polar representation can be used to assess global vasomotion, e.g., it can be assessed by a closeness operation utilizing the entire Polar image.

After two dimensional shift evaluation is performed, as discussed above, the location of the maximum in matrix C(shiftX, shiftY) on the θ-axis is utilized for rotational stabilization. This leaves the location of the extremum on the r-axis, which can be used as an indication of global vasomotion. Thus, global vasomotion monitoring is a by-product of two dimensional shift evaluation in the Polar image.

Each pair of successive images produce a value indicative of the vasomotion. Both the magnitude and the sign of the resulting shift between images characterize the change in the vessel, i.e., vasomotion. Negative shifts indicate dilation, and positive shifts indicate contraction. The magnitude of the value indicates the magnitude of the vasomotion change.

Figure 6:
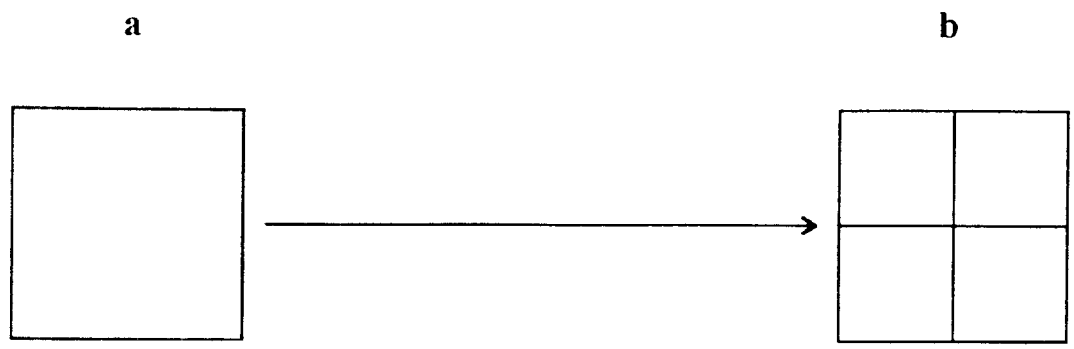
FIG. 6 shows an image divided into four sections for processing according to the present invention.

Under certain circumstances motion or vasomotion may not be uniform/rigid although confined to the plane of the image, i.e., transverse. To determine the type of motion or vasomotion, the image may be divided into sections and global stabilization evaluation performed on each of these sections. By examining the indicated shifts of these sections relative to the corresponding sections in the predecessor image, a determination can be made as to the type of motion. For example, as shown in FIG. 6, the image in FIG. 6(a) can be divided into four sections as shown in FIG. 6(b). Shift evaluation can be performed separately on each of the four sections. Comparison between the results of the shift evaluation for each of the four sections can possibly identify the type of actual motion. Thus, the type of stabilization applied can be varied depending on the type of motion detected.

Stabilization for local motion is achieved by performing closeness operations on a localized basis. Small portions of the predecessor image A ("template" regions) and small portions of the current image B ("search" regions) participate in the local stabilization process. Sometimes, it is best to perform local stabilization after global stabilization has been performed.

During local stabilization, template regions in the predecessor image (A) are shifted within search regions and compared, using closeness operations to template sized regions in the current image (B). Each pixel, in the (newly) formed stabilized image (B') will be assigned a new value based on the results of the search and closeness evaluation performed.

Local stabilization is illustrated by the following example in which the template region is a 1×1 pixel region, i.e., a single pixel, the search region is a 3×3 pixel region and the closeness operation is SAD. In the following diagram, the pixel valued 3 in A and the pixel valued 9 in B are corresponding pixels. The 3×3 pixel neighborhood of the pixel valued 9 is also illustrated.

| Pixel in A ("template" region) | Pixels in B (3 × 3 "search" region) | B' |
|---|---|---|
| 3 | 1 10 10<br>7 9 50<br>11 7 60 | 1 |

In this example, according to the conditions described above the 'template' pixel valued 3 is compared using SAD to all pixels found in the 3×3 search region around the pixel valued 9. The pixel valued 1 at the top left corner of the search region will achieve the minimal SAD value (|1−3|=2) out of all the possibilities in the search region. As a result, in the newly formed stabilized image (B'), the pixel corresponding in location to pixels valued 3 and 9 will be assigned the value of 1.

In general, the dimensions of the template and search region can be varied along with the closeness operations used. The actual value which is assigned to the pixel of the newly formed stabilized image (B') need not necessarily be an actual pixel value from the current image B (as illustrated in the example) but some function of pixel values. It is important to note that as a result of local stabilization, as opposed to the global/rigid methods, the "composition" of the image, i.e., the internal relationship between pixels, and their distribution in the stabilized image, changes in relation to the original image. Local stabilization can be implemented on both the Polar and Cartesian representations of the image.

Figure 7:
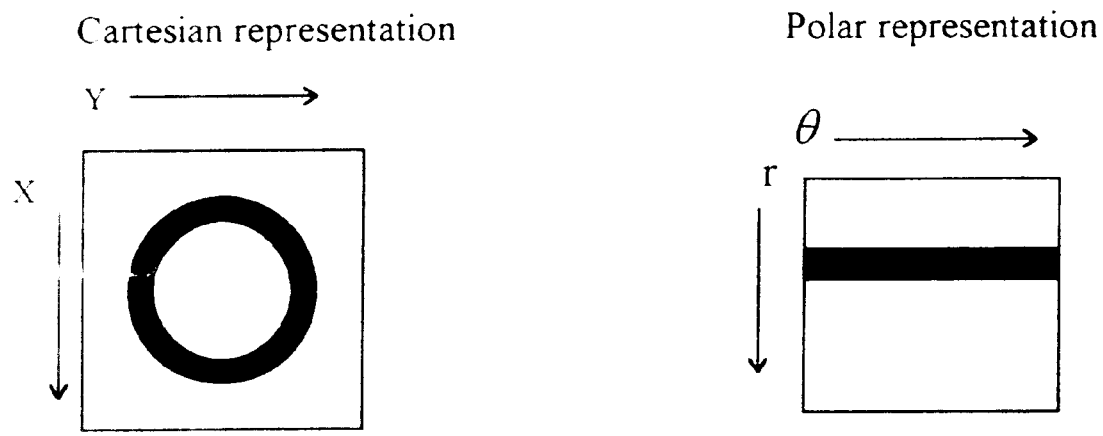
FIG. 7 shows a vessel, in both Cartesian and Polar coordinates, in which local vasomotion has been detected.
Figure 7:
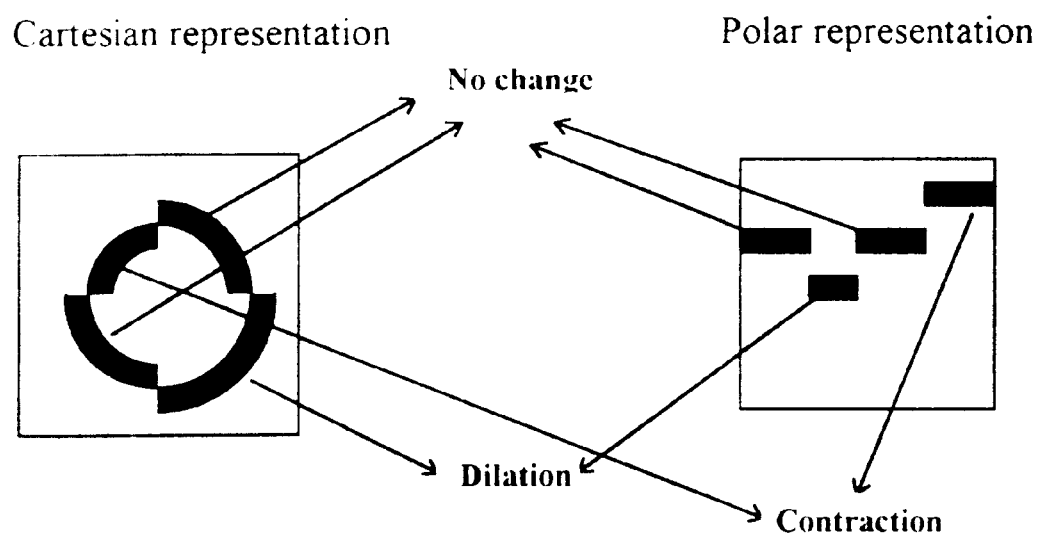

FIG. 7 shows a vessel, in both Cartesian and Polar coordinates, in which local vasomotion has been detected.

When local vasomotion is detected, it is an indication that some parts of the cross-section of the vessel are behaving differently than other parts of the cross-section.

FIG. 7(a) shows a baseline figure of the vessel prior to local vasomotion. FIG. 7(b) shows an example of local vasomotion. As indicated in both the Cartesian and Polar representations, four distinct parts of the vessel behave differently: two segments of the vessel do not change caliber, or do not move relative to their corresponding segments in the predecessor image; one segment contracts, or moves up; and one segment dilates, or moves down.

As can be observed, global vasomotion evaluation methods are not appropriate for evaluating local vasomotion because the vessel does not behave in a uniform manner. If global vasomotion evaluation was to be applied, for example, on the example shown in FIG. 7, it might detect overall zero vasomotion, i.e. the contraction and dilation would cancel each other.

Therefore, local vasomotion evaluation methods must be utilized. This may be achieved by separately evaluating vasomotion in each Polar vector, i.e., in each θ (or Y) vector. Closeness operations are applied using one dimensional shifts in corresponding Polar vectors. For example, if closeness is utilized with cross-correlation, then the following operation illustrates how this is accomplished using one dimensional shifts.

$$C(shiftX, Y) = \sum_x B(x - shiftX, y) * A(x, y)$$

where:

$A$ = predecessor image matrix;

$B$ = current image matrix;

$*$ = multiplication of pixel by corresponding pixel;

$\sum$ = sum of pixels in the matrix of the Polar vector;

$C$ = two dimensional matrix of correlation coefficient

As can be seen, shifting is performed along one axis (X or r-axis) for each and every Polar vector (θ or Y vector). The values assigned in each vector for shift evaluation may not be the actual values of the images but, for example, each pixel in the vector can be assigned the average of its lateral neighbors, i.e., A(X, Y) will be assigned, for example, the average of A(X, Y−1), A(X, Y) and A(X, Y+1). The same goes for B(shiftX, Y). This can make the cross-correlation process more robust to noise.

A two dimensional matrix (C(shiftX, Y)) is formed. Each column in the matrix stores the results of closeness/similarity operations performed between corresponding Polar vectors from the current image and the predecessor image. This operation could also have been implemented using FFT.

After formation of the matrix, the location of the extremum (maximum in the cross-correlation operation) in each column is detected. This extremum location indicates the match between the current Polar vector and its predecessor. Thus, the vasomotion in each vector can be characterized, i.e., the radial movement in each specific angular sector of the vessel.

This information can be used to display the local vasomotion, it can be added up from some or all Polar vectors and averaged to determine an average value for the vasomotion, or it can be used for other purposes. Therefore, by evaluating local vasomotion, both local and global vasomotion can be evaluated.

To be effectively used and/or expressed as quantitative physiological parameters, the magnitude of vasomotion must relate in some fashion to the vessel's actual caliber. Thus, measurements of vasomotion monitoring should generally be used in conjunction with automatic or manual measurements of the vessel's caliber Besides for true vasomotion, Cartesian displacement may also be detected as vasomotion. This is because Cartesian displacement, when expressed in Polar coordinates, results in shifts along both the r and θ axes. To distinguish true vasomotion from Cartesian displacement, shift evaluation in the Cartesian image must indicate no, or little motion. If Cartesian displacement is detected, then it must first be stabilized. Thereafter, the Cartesian coordinates may be converted back into Polar coordinates for vasomotion evaluation. This will allow greater success and provide more accurate results when determining actual vasomotion.

Figure 8A:
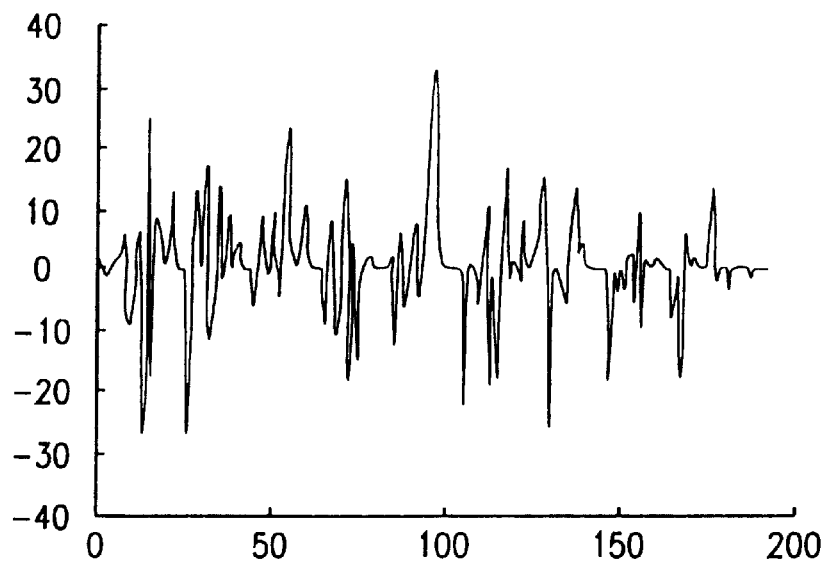
FIG. 8 illustrates the results of local vasomotion monitoring in a real coronary vessel in graphical form.
Figure 8B:
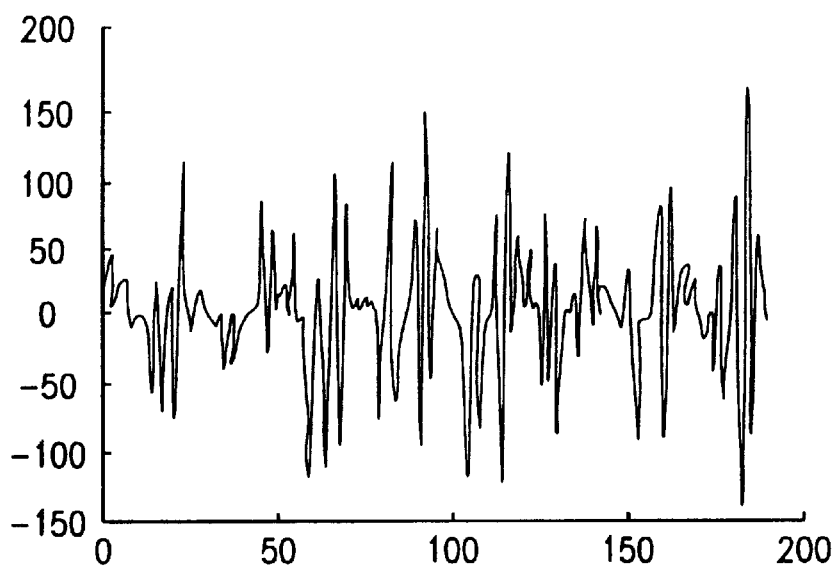

The graphs in FIG. 8 illustrate the results of local vasomotion monitoring in a human coronary vessel in vivo. Local vasomotion monitoring was performed twice in approximately the same segment of the vessel, and consisted of 190 successive images as shown (X-axis) in FIGS. 8(a) and 8(b). The difference between the two graphs is that the vasomotion evaluation shown in FIG. 8(a) was performed prior to treatment of the artery, i.e., pre-intervention, while the vasomotion evaluation shown in FIG. 8(b) was performed after treatment of the artery, i.e., post-intervention.

In every image, vasomotion was assessed locally in every Polar vector and then all detected individual shifts were added and averaged to produce a single global vasomotion indication (Y-axis) for each image, i.e., an indication for vasomotion activity.

The units on the Y-axis do not have a direct physiological meaning because the actual caliber of the vessel was not calculated, but the relationship between the values in FIGS. 8(a) and 8(b) have a meaning because they were extracted from the same vessel. Thus, important information may be derived from these figures. Note how the vasomotion increased after treatment (maximal vasomotion from approximately 40 to approximately 150). Therefore, even though vasomotion was not fully quantified, a change in physiology (probably linked to the treatment) has been demonstrated.

Cardiovascular periodicity may be monitored solely based on information stored in IVUS images, thereby eliminating the need for an ECG or any other external signal. This means that a link can be established between every image and its respective temporal phase in the cardiovascular cycle without need for an external signal. Once this linkage is established, then monitoring can substitute the ECG signal in a large number of utilities which require cardiac gating. This monitoring may be accomplished using closeness operations between successive images. Moreover, the same closeness operations can produce information regarding the quality of IVUS images and their behavior.

The cardiac cycle manifests itself in the cyclic behavior of certain parameters that are extracted by IVUS images. If the behavior of these parameters are monitored, then the periodicity of the cardiac cycle can be determined. Knowing the frame acquisition rate will also allow the determination of the cardiovascular cycle as a temporal quantity.

The closeness between successive IVUS images is a parameter which clearly behaves in a periodic pattern. This is a result of the periodicity of most types of inter-image motion that are present. A closeness function may be formed in which each value results from a closeness operation between a pair of successive images. For example, a set of ten images will produce nine successive closeness values.

The closeness function can be derived from a cross-correlation type operation, SAD operation or any other type of operation that produces a closeness type of function. Normalized cross-correlation produces very good results when used for monitoring periodicity.

The following formula shows the formula for the cross-correlation coefficient (as a function of the Nth image) for calculating the closeness function:

$$Correlation\_function(N) =$$

$$\sum_{x,y} = B(x,y) * A(x,y) \Big/ \sqrt{\left(\sum_{x,y} A(x,y)^2 * \sum_{x,y} B(x,y)^2\right)}$$

where:

$Correlation\_function(N)$ = one dimensional function producing one value for every pair of images;

$A$ = predecessor image matrix (the Nth image);

$B$ = current image matrix (the Nth + 1 image);

$*$ = multiplication of pixel by corresponding pixel;

$\sum$ = sum on all pixels in matrix.

The correlation coefficient is a byproduct of the stabilization process, because the central value (shiftX=0, shiftY=0) of the normalized cross-correlation matrix (C(shiftX, shiftY)) is always computed. This holds true for all types of closeness functions used for stabilization. The central value of the closeness matrix (C(shiftX=0, shiftY=0)), either cross-correlation or another type of operation used for stabilization, can always be used for producing a closeness function.

The closeness function can also be computed from images which are shifted one in relation to another, i.e., the value used to form the function is C(shiftX, shiftY) where shiftX and shiftY are not equal to zero. The Closeness function need not necessarily be formed from whole images but can also be calculated from parts of images, either corresponding or shifted in relation to one another.

Figure 9:
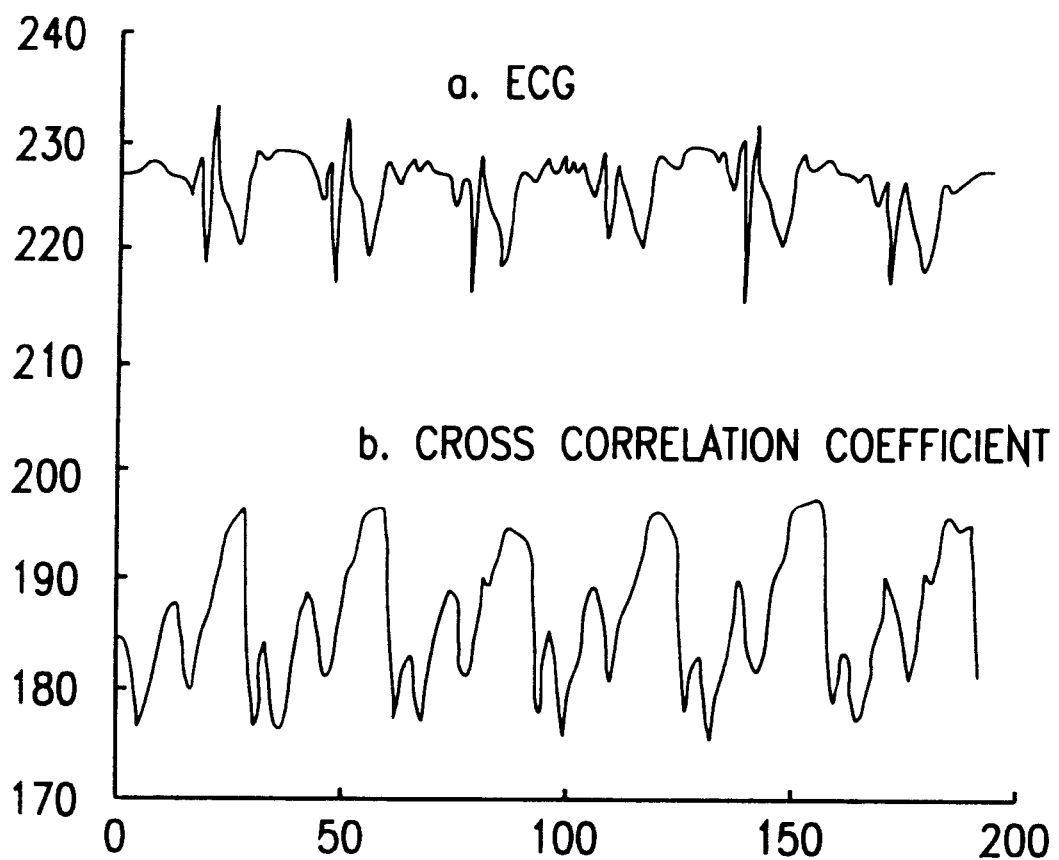
FIG. 9 shows an ECG and cross-correlation coefficient plotted graphically in synchronous fashion.

FIG. 9 shows an ECG and cross-correlation coefficient plotted graphically in synchronous fashion. Both curves are related to the same set of images. FIG. 9(a) shows a graph of the ECG signal and FIG. 9(b) shows a graph of the cross-correlation coefficient derived from successive IVUS images. The horizontal axis displays the image number (a total of 190 successive images). As can be observed, the cross-correlation coefficient function in FIG. 9(b) shows a periodic pattern, and its periodicity is the same as that displayed by the ECG signal in FIG. 9(a) (both show approximately six heart beats).

Monitoring the periodicity of the closeness function may be complicated because the closeness function does not have a typical shape, it may vary in time, it depends on the type of closeness function used, and it may vary from vessel segment to vessel segment and from subject to subject.

To monitor the periodicity of the closeness function continuously and automatically a variety of methods may be employed. One method, for example, is a threshold type method. This method monitors for a value of the closeness function over a certain value known as a threshold. Once this value is detected, the method monitors for when the threshold is again crossed. The period is determined as the difference in time between the crossings of the threshold. An example of this method is shown in FIG. 10 as a table. The table shows a group of cross-correlation coefficient values (middle row) belonging to successive images (numbers 1 through 10 shown in the top row). If the threshold, for example, is set to the value of 0.885, then this threshold is first crossed in the passage from image #2 to image #3. The threshold is crossed a second time in the passage from image #6 to image #7. Thus, the time period of the periodicity is the time taken to acquire 7−3=4 images.

Another method that can be used to extract the cardiac periodicity from the closeness curve is internal cross-correlation. This method utilizes a segment of the closeness function, i.e., a group of successive values. For example, in the table shown in FIG. 10, the segment may be comprised of the first four successive images, i.e., images #1 through #4. Once a segment is chosen, it is cross-correlated with itself, producing a cross-correlation value of 1. Next, this segment is cross-correlated with a segment of the same size extracted from the closeness function, but shifted one image forward. This is repeated, with the segment shifted two images forward, and so on. In the example shown in FIG. 10, the segment {0.8, 0.83, 0.89, 0.85} would be cross-correlated with a segment shifted by one image {0.83, 0.89, 0.85, 0.82}, then the segment {0.8, 0.83, 0.89, 0.85} would be cross-correlated with a segment shifted by two images {0.89, 0.85, 0.82, 0.87}, and so on. The bottom row of the table in FIG. 10 shows the results of these internal cross-correlations. The first value of 1 is a result of the cross-correlation of the segment with itself. These cross-correlation values are examined to determine the location of the local maxima. In this example, they are located in image #1 and image #5 (their values are displayed in bold). The resulting periodicity is the difference between the location of the local maxima and the location from which the search was initiated (i.e., image #1). In this example, the periodicity is the time that elapsed from the acquisition of image #1 to image #5, which is 5−1=4 images. Once a period has been detected, the search begins anew using a segment surrounding the local maximum, e.g., image #5. In this example, for example, the new segment could be the group of closeness values belonging to images #4 through #7.

Due to the nature of the type of calculation involved, the internal cross-correlation operation at a certain point in time requires the closeness values of images acquired at a future time. Thus, unlike the threshold method, the closeness method requires the storage of images (in memory) and the periodicity detection is done retrospectively. The cardiac periodicity can also be monitored by transforming the closeness curve into the temporal frequency domain by the Fourier transform. In the frequency domain the periodicity should be expressed as a peak corresponding to the periodicity. This peak can be detected using spectral analysis.

The closeness function can provide additional important information about IVUS images which cannot be extracted from external signals, such as ECG, that are not derived from the actual images. The behavior of this function can indicate certain states in the IVUS images or image parts used to form the closeness function. Important features in the closeness function which are indicative of the state of the IVUS images are the presence of periodicity and the "roughness" of the closeness function. Normal IVUS images should exhibit a relatively smooth and periodic closeness function as displayed, for example, in FIG. 9(b).

Figure 11:
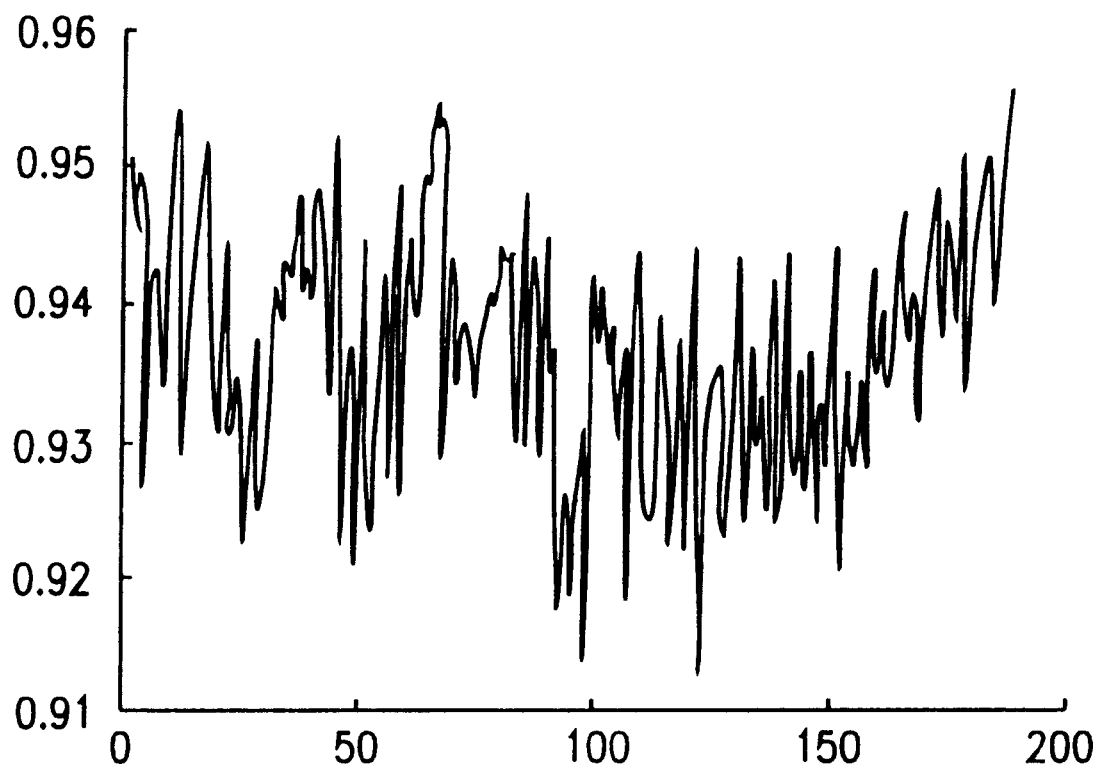
FIG. 11 shows a plot of a cross-correlation coefficient indicating an artifact in IVUS images.

However, if "roughness" and/or periodicity are not present then this could indicate some problem in the formation of IVUS images, i.e., the presence of an artifact in the image formation caused by, for example, either a mechanical or electronic malfunction. The following figure helps to illustrate this. FIG. 11 shows a graph of the cross-correlation coefficient derived from successive IVUS images. This graph is analogues, in its formation, to the cross-correlation plot in FIG. 9(b), but in this example it is formed by a different imaging catheter used in a different subject.

In this example, it is clear that the closeness function does not exhibit clear periodicity nor does it have a smooth appearance but rather a rough or spiky appearance. In this case the behavior of the closeness graph was caused by the non-uniformity of the rotation of the IVUS transducer responsible for emitting/collecting the ultrasonic signals displayed in the image. This type of artifact sometimes appears in IVUS catheter-transducer assemblies in which there are moving mechanical parts.

The closeness function, when considered to reflect normal imaging conditions, can serve for a further purpose. This is linked with the location of the maxima in each cycle of the closeness function. Locating these maxima may be important for image processing algorithms which process several successive images together. Images found near maxima images tend to have high closeness and little inter-image motion, one in relation to the other. Additionally, if images belonging to the same phase of successive cardiac cycles are required to be selected, it is usually best to select them using the maxima (of the closeness function) in each cycle.

In one display method, for example, these images are projected onto the display and the gaps are filled in by interpolated images. By this display method all types of periodic motion can be stabilized.

The shift logic stage in the stabilization process can also make use of cardiovascular periodicity monitoring. If drift is to be avoided, the accumulated shift after each (single) cardiac cycle should be small or zero, i.e., the sum of all shifts over a period of a cycle should result in zero or near zero. This means that the drift phenomena can be limited by utilizing shift logic which is coupled to the periodicity monitoring.

Figure 12:
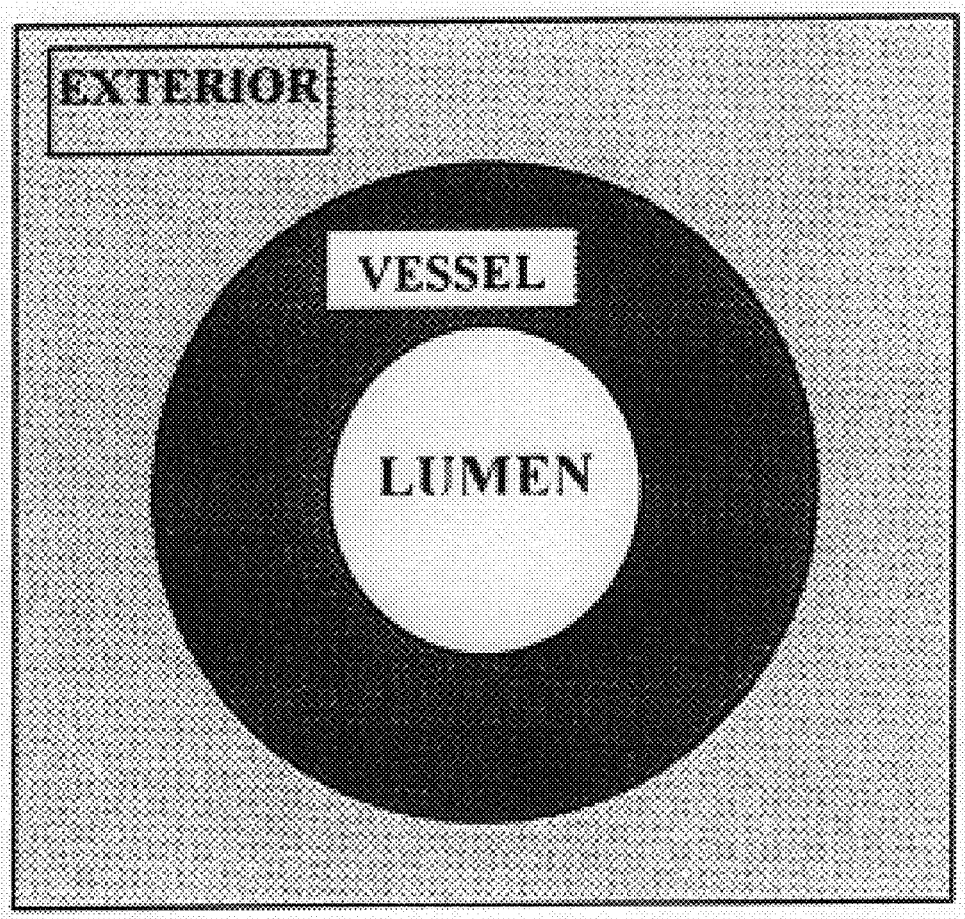
FIG. 12 shows an IVUS images divided into three basic parts: the lumen through which fluid flows; the actual vessel; and the surrounding tissue.

Referring now to FIG. 12, most IVUS images can be divided into three basic parts. The central area (around the catheter), labeled as Lumen in FIG. 12, is the actual lumen or interior passageway (cavity) through which fluid, e.g., blood flows. Around the lumen, is the actual vessel, labeled Vessel in FIG. 12, composed of several layers of tissue and plaque (if diseased). Surrounding the vessel is other tissue, labeled Exterior in FIG. 12, i.e., muscle or organ tissue, for example, the heart in the coronary vessel image.

When IVUS images are viewed dynamically (i.e., in film format), the display of the interior, where the blood flows, and of the exterior surrounding the vessel, usually shows a different temporal behavior than the vessel itself.

Automatically monitoring the temporal behavior of pixels in the dynamic IVUS image would allow use of the information extracted by the process to aid in interpretation of IVUS images. This information can be used to enhance IVUS displays by filtering and suppressing the appearance of fast changing features, such as fluid, e.g., blood, and the surrounding tissue, on account of their temporal behavior. This information can also be used for automatic segmentation, to determine the size of the lumen automatically by identifying the fluid, e.g., blood, and the surrounding tissue based on the temporal behavior of textural attributes formed by their composing pixels.

To accomplish automatic monitoring of temporal behavior there must be an evaluation of the relationship between attributes formed by corresponding pixels belonging to successive images. Extraction of temporal behavior bears resemblance to the methods used for closeness operations on a localized basis, as described previously.

High temporal changes are characterized by relatively large relative gray value changes of corresponding pixels, when passing from one image to the next. These fast temporal changes may be suppressed in the display by expressing these changes through the formation of a mask which multiplies the original image. This mask reflects temporal changes in pixel values. A problem that arises in this evaluation is determining whether gray value changes in corresponding pixel values are due to either flow or change in matter, or movements of the vessel/catheter. By performing this evaluation on stabilized images overcomes or at least minimizes this problem.

The following definitions apply:

B=current (stabilized or non-stabilized) image;
A=predecessor (stabilized or non-stabilized) image;
C=successor (stabilized or non-stabilized) image;
abs=absolute value.

The matrices used can be either in Cartesian or Polar form.

The following operation, resulting in a matrix D1, shall be defined as follows: D1 is a matrix, in which each pixel with coordinates X, Y is the sum of the absolute differences of its small surrounding neighborhood, e.g., 9 elements (X−2:X+2, Y−2:Y+2—a 3×3 square), extracted from images A and B, respectively.

For example, the following illustration shows corresponding pixels (in bold) and their close neighborhood in matrices A and B.

| A | B | D1 |
|---|---|---|
| 1 4 51 | 3 6 8 | 190 |
| 6 7 15 | 3 4 70 | |
| 3 5 83 | 2 1 6 | |

The pixel in matrix D1, with the location corresponding to the pixels with value 4 (in B) and 7 (in A) will be assigned the following value:

$$abs(1-3)+abs(4-6)+abs(51-8)+abs(6-3)+abs(7-4)+abs(15-70)+abs(3-2)+abs(5-1)+abs(83-6)=190$$

D2 is defined similarly but for matrices B and C.

D1 and D2 are, in effect, difference matrices which are averaged by using the 3×3 neighborhood in order to diminish local fluctuations or noise. Large gray value changes between images A and B or between B and C will be expressed as relatively high values in matrices D1 and D2 respectively.

A new matrix, Dmax is next formed, in which every pixel is the maximum of the corresponding pixels in matrices D1 and D2:

$$D\text{max}=\max(D1,D2)$$

where:

max(D1, D2)=each pixel in Dmax holds the highest of the two corresponding pixels in D1 and D2.

Thus, the single matrix Dmax particularly enhances large pixel changes between matrices A, B and C. A mask matrix (MD), is then formed from Dmax by normalization, i.e., each pixel in Dmax is divided by the maximal value of Dmax. Therefore, the pixel values of the mask MD range from zero to one.

The role of the mask is to multiply the current image B in the following manner, forming a new matrix or image defined as BOUT:

$$BOUT = (1-MD^n) * B$$

where:
B=original current image;
BOUT=the new image;
$^n$=each pixel in the matrix MD is raised to the power of n. n is generally a number with a value, for example, of 2–10;
$1-MD^n$=a matrix in which each pixel's value is one minus the value of the corresponding pixel in MD.

By performing the subtraction $1-MD^n$, small values of MD which reflect slow changing features become high values in $1-MD^n$. Moreover, the chance that only slow changing features will have high values is increased because of the prior enhancement of high MD values (by forming MD as a maximum between matrices D1 and D2).

The multiplication of the mask ($1-MD^n$) by the current image B, forms a new image BOUT in which the appearance of slow changing pixels are enhanced while fast changing pixels' values are decreased. The number n determines how strong the suppression of fast changing features will look on the display.

Figure 13:
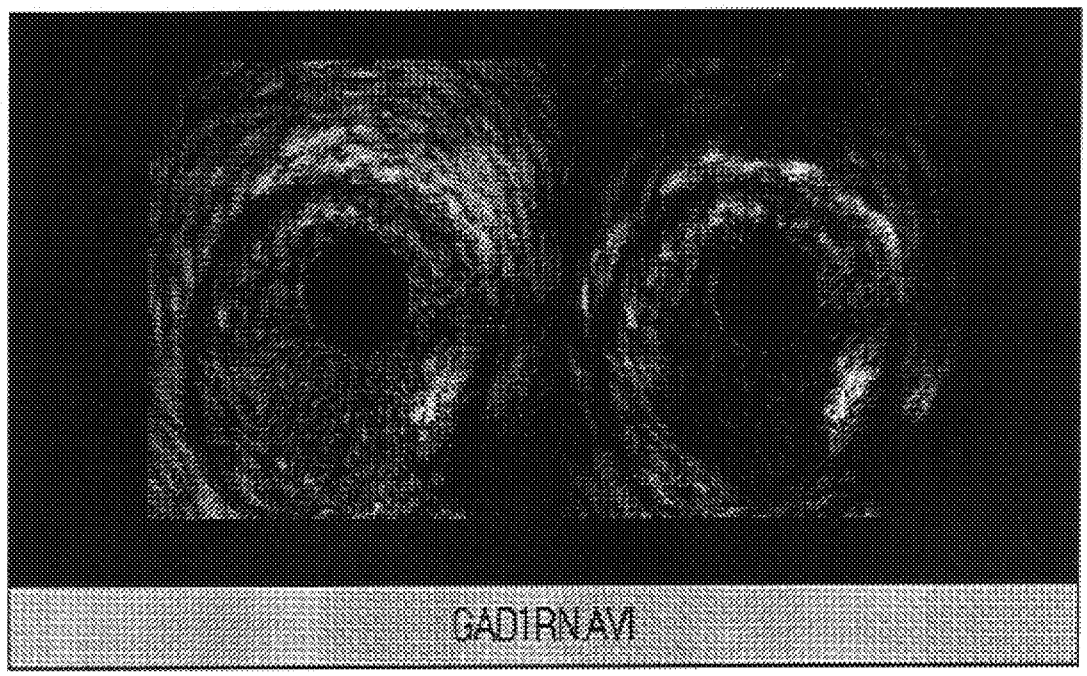
FIG. 13 illustrates the results of temporal filtering.

FIG. 13 illustrates the results of temporal filtering. The left image is an original IVUS image (i.e., matrix B) from a coronary vessel, as it would look on the current display. The right image has undergone the processing steps described above, i.e., temporal filtering (matrix BOUT). Note that in the right image, blood and the surrounding tissue is filtered (suppressed) and lumen and vessel borders are much easier to identify.

Automatic segmentation differentiates fluid, e.g., blood and exterior, from the vessel wall based on the differences between the temporal behavior of a textural quality. As in the case of temporal filtering, this method is derived from the relationship between corresponding pixels from a number of successive images. If pixel values change because of inter-image motion, then performance of the algorithm will be degraded. Performing stabilization prior to automatic segmentation will overcome, or at least minimize this problem.

As in the case of temporal filtering, the following definitions shall apply:

B=current (stabilized or non-stabilized) image;
A=predecessor (stabilized or non-stabilized) image;
C=successor (stabilized or non-stabilized) image.

The matrices can be either in Cartesian or Polar form.

The textural quality can be defined as follows: Suppose the four nearest neighbors of a pixel with value "a" are "b," "c," "d" and "e," then the classification of "a" will depend on its relations with "b," "c," "d" and "e." This can be shown with the following illustration:

$$b$$
$$c \quad a \quad d$$
$$e$$

The following categories can now be formed:
In the vertical direction:

if a>b and a>e then "a" is classified as belonging to the category I;

if a>b and a<e then "a" is classified as belonging to the category II;
if a<b and a<e then "a" is classified as belonging to the category III;
if a<b and a>e then "a" is classified as belonging to the category IV;
if a=b or a=e then "a" is classified as belonging to the category V.

In the horizontal direction:
if a>c and a>d then "a" is classified as belonging to the category I;
if a>c and a<d then "a" is classified as belonging to the category II;
if a<c and a<d then "a" is classified as belonging to the category III;
if a<c and a>d then "a" is classified as belonging to the category IV;
if a=c or a=d then "a" is classified as belonging to the category V.

The vertical and horizontal categories are next combined to form a new category. As a result, pixel "a" can now belong to 5×5=25 possible categories. This means that the textural quality of "a" is characterized by its belonging to one of those (25) categories.

For example, in the following neighborhood:

$$7$$
$$10 \quad 10 \quad 14$$
$$3$$

Pixel "a"=10 is classified as belonging to the category which includes category I vertical (because 10>7 and 10>3) and category V horizontal (because 10=10). However, if pixel "a" would have been situated in the following neighborhood:

$$7$$
$$11 \quad 10 \quad 14$$
$$3$$

it would have been classified as belonging to a different category because its horizontal category is now category III (10<11 and 10<14).

By determining the relationship of each pixel to its close neighborhood a textural quality has been formed which classifies each pixel into 25 possible categories. The number of categories may vary (increased or decreased), i.e., for example, by changing the categorizing conditions, as may the number of close neighbors used, for example, instead of four, eight close neighbors may be used.

The basic concept by which the textural changes are used to differentiate fluid, e.g., blood, from the vessel is by monitoring the change in categories of corresponding pixels in successive images. To accomplish this the category in each and every pixel in matrices A, B and C are determined. Next, corresponding pixels are each tested to see if this category has changed. If it has, the pixel is suspected of being a fluid, e.g., blood, or surrounding tissue pixel. If it has not changed, then the pixel is suspected of being a vessel pixel.

The following example shows three corresponding pixels (with values 8, 12 and 14) and their neighborhoods in successive matrices A, B and C.

| A | B | C |
|---|---|---|
| 5 | 9 | 1 |
| 9 8 11 | 19 12 13 | 21 14 17 |
| 23 | 100 | 20 |

In this example, the category of the pixel valued 12 (in B) is the same as in A and C, so it will be classified as a pixel with a higher chance of being a vessel wall pixel. If, however, the situation was as shown below (20 in C changes to 13):

| A | B | C |
|---|---|---|
| 5 | 9 | 1 |
| 9 8 11 | 19 12 13 | 21 14 17 |
| 23 | 100 | 13 | then pixels 8 in A and 12 in B have the same categories, but 14 in C has a different category as in the prior example. As a result, pixel 12 in B will be classified as a pixel with a higher chance of being a fluid (lumen), i.e., blood, or exterior tissue pixel.

The classification method described so far monitors the change in the texture or pattern associated with the small neighborhood around each pixel. Once this change is determined as described above, each pixel can be assigned a binary value. For example, a value of 0, if it is suspected to be a vessel pixel, or a value of 1, if it is suspected to be a blood pixel or a pixel belonging to the vessel's exterior. The binary image, serves as an input for the process of identification of the lumen and the original pixel values cease to play a role in the segmentation process.

Identification of the lumen using the binary image is based on two assumptions which are generally valid in IVUS images processed in the manner described above. The first, is that the areas in the image which contain blood or are found on the exterior of the vessel are characterized by a high density of pixels with a binary value of 1 (or a low density of pixels with a value of zero). The term density is needed because there are always pixels which are misclassified. The second assumption, is that from a morphological point of view, connected areas of high density of pixels with the value of 1 (lumen) should be found around the catheter and surrounded by connected areas of low density of pixels with the value of 1 (vessel) which are in turn, surrounded again by connected areas of high density of pixels with the value of 1 (vessel's exterior). The reason for this assumption is the typical morphological arrangement expected from a blood vessel.

These two assumptions form the basis of the subsequent processing algorithm which extracts the actual area associated with the lumen out of the binary image. This algorithm can utilize known image processing techniques, such as thresholding the density feature in localized regions (to distinguish blood/exterior from vessel ) and morphological operators such as dilation or linking to inter-connect and form a connected region which should represent the actual lumen found within the vessel wall limits.

Figure 14:
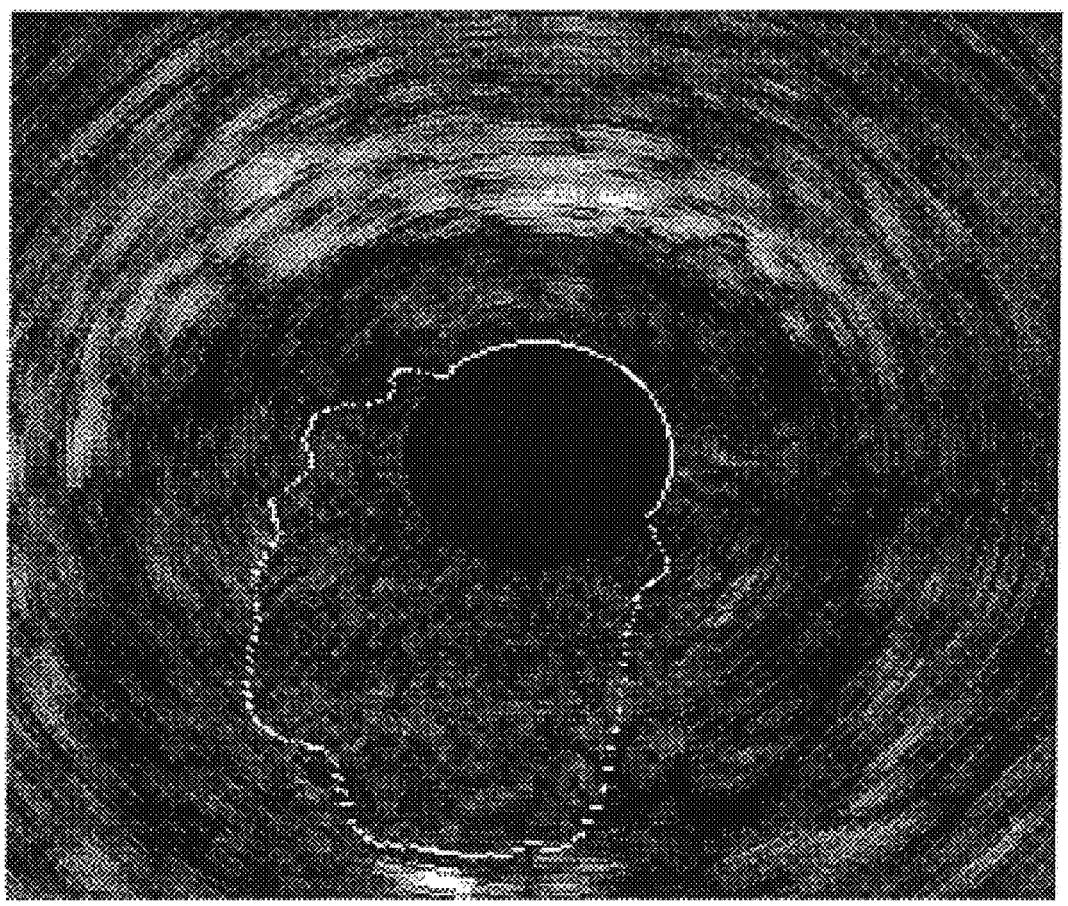
FIG. 14 shows an image of the results of the algorithm for automatic extraction of the lumen.

FIG. 14 shows an image of the results of the algorithm for automatic extraction of the lumen. The image is an original IVUS image (for example, as described above as image B) and the lumen borders are superimposed (by the algorithm) as a bright line. The algorithm for the extraction of the lumen borders was based on the monitoring of the change in the textural quality described above, using three successive images.

The examples described above of temporal filtering and automatic segmentation include the use of two additional images (for example, as described above as images A and C) in addition to the current image (for example, as described above as image B). However, both of these methods could be modified to utilize less (i.e., only one additional image) or more additional images.

The performance of the two methods described above will be greatly enhanced if combined with cardiovascular periodicity monitoring. This applies, in particular, to successive images in which cardiovascular periodicity monitoring produces high inter-image closeness values. Those images usually have no inter-image motion. Thus, most reliable results can be expected when successive images with maximal inter-image closeness are fed as inputs to either temporal filtering or automatic segmentation.

During treatment of vessels using catheterization, it is a common practice to repeat IVUS pullback examinations in the same vessel segment. For example, a typical situation is first to review the segment in question, evaluate the disease (if any), remove the IVUS catheter, consider therapy options, perform therapy and then immediately after (during the same session) examine the treated segment again using IVUS in order to assess the results of therapy.

To properly assess the results of such therapy, corresponding segments of the pre-treatment and post-treatment segments which lie on the same locations along the length of the vessel, i.e., corresponding segments, should be compared. The following method provides for matching, i.e., automatic identification (registration) of corresponding segments.

To accomplish matching of corresponding segments, closeness/similarity operations are applied between images belonging to a first group of successive images, i.e., a reference segment, of a first pullback film and images belonging to a second group of successive images of a second pullback film. Matching of the reference segment in the first film to its corresponding segment in the second film is obtained when some criteria function is maximized.

From either one of the two films a reference segment is chosen. The reference segment may be a group of successive images representing, for example, a few seconds of film of an IVUS image. It is important to select the reference segment from a location in a vessel which is present in the two films and has undergone no change as a result of any procedure, i.e., the reference segment is proximal or distal to the treated segment.

As an example, the table in FIG. 15 will help clarify the method for matching of corresponding segments.

The left column shows the time sequence of the first film, in this case the film consists of twenty successive images. The middle column, shows the reference segment which is selected from the second film and consists of 10 successive images. The right column lists the 10 successive images from the first film (#5–#14) which actually correspond to (or match) the images of the reference segment from the second film (#1–#10). The purpose of the matching process is to actually reveal this correspondence.

Once a reference segment is chosen, it is shifted along the other film, one image (or more) each time, and a set of stabilization and closeness operations are performed between the corresponding images in each segment. The direction of the shift depends on the relative location of the reference segment in the time sequence of the two films. However, in general, if this is not known, the shift can be performed in both directions.

In the example of FIG. 15:
r=reference segment; and
f=first film,
the first set of operations will take place between the images comprising the following pairs: r#1–f#1, r#2–f#2, r#3–f#3, . . . , r#10–f#10.

The second set of operations will take place between the images comprising the following pairs: r#1–f#2, r#2–f#3, r#3–f#4, . . . , r#10–f#11.

The third set of operations will take place between the images comprising the following pairs: r#1–f#3, r#2–f#4, r#3–f#5, . . . , f#10–f#12, and so on, etc. As can be observed in this example, the shifting is performed, by a single image each time and in one direction only.

For example, the following operations between the images in each pair may be performed. First, an image from the reference segment is stabilized for rotational and Cartesian motion, in relation to its counterpart in the first film. Then closeness operations are performed between the images in each pair. This operation can be, for example, normalized cross-correlation (discussed above in relation to periodicity detection). Each such operation produces a closeness value, for example, a cross-correlation coefficient when normalized cross-correlation is used. A set of such operations will produce a number of cross-correlation values. In the example shown in the table of FIG. 15, each time the reference segment is shifted, ten new cross-correlation coefficients will be produced.

The closeness values produced by a set of operations can then be mapped into some type of closeness function, for example, an average function. Using the above example, the cross-correlation coefficients are summed up and then divided by the number of pairs, i.e., ten. Each set of operations results therefore, in a single value, i.e., an average closeness, which should represent the degree of closeness between the reference segment and its temporary counterpart in the first film. Thus, the result of the first set of operations will be a single value, the result of the second set of operations will be another value, etc.

We can expect that the maximal average closeness will occur as a result of the operations performed between segments which are very alike, i.e., corresponding or matching segments.

In the above example of FIG. 15, these segments should be matched during the fifth set of operations which take place between the images comprising the following pairs: r#1–f#5, r#2–f#6, r#3–f#7, . . . , r#10–f14.

The maximal average closeness should, therefore, indicate corresponding segments because each pair of images are, in fact, corresponding images, i.e., they show the same morphology. The criteria might not, however, follow this algorithm. It may, for example, take into account the form of the closeness function, derived from many shifted segment positions instead of using only one of its values which turns out to be the maximum.

Once corresponding segments are identified, the complete first and second films may be synchronized one in relation to the other. This will be a result of an appropriate frame shift, revealed by the matching process, implemented in one film in relation to the other. Thus, when watching the two films side by side, the pre-treated segment will appear concurrently with the post-treated section.

Besides for synchronizing the corresponding segments, the above operation also stabilizes the corresponding segments one in relation to the other. This further enhances the ability to understand the changes in morphology. Thus, even though when the catheter is reinserted in the vessel its position and orientation are likely to have changed, nevertheless, the images in the pre-treatment and post-treatment films will be stabilized in relation to each other.

The number of images used for the reference segment may vary. The more images used in the matching process, the more robust and less prone to local errors it will be. However, the tradeoff is more computational time required for the calculations for each matching process as the number of pairs increases.

It is important in acquiring the pullback films that the pullback rate remains stable and is known. It is preferred that the pullback rate be identical in the two acquisitions.

Many different variations of the present invention are possible. The various features described above may be incorporated individually and independently of one another. These features may also be combined in various groupings.

What is claimed is:

1. An apparatus for performing an intravascular ultrasound imaging via an ultrasound signal transmitter and detector capable of being placed within a bodily lumen, comprising:

an arrangement for detecting ultrasound signals;

an arrangement for deriving a first image from a first set of detected ultrasound signals;

an arrangement for processing and digitizing the first set of detected ultrasound signals;

an arrangement for deriving a first two-dimensional array from the digitized first set of detected ultrasound signals, the first two-dimensional array including a first plurality of elements, wherein the first image is configured as the first two-dimensional array;

an arrangement for deriving a second image from a second set of the detected ultrasound signals;

an arrangement for processing and digitizing the second set of detected ultrasound signals;

an arrangement for deriving a second two-dimensional array from the digitized second set of detected ultrasound signals, wherein the second image is configured as the second two-dimensional array, the second two-dimensional array including a second plurality of elements, each one of the first plurality of elements and the second plurality of elements representing a detected ultrasound signal from a predetermined spatial location; and an arrangement for performing a shift evaluation of the second image in relation to the first image in order to detect a motion.

2. The apparatus according to claim 1, wherein:

each one of the first two dimensional array and the second two dimensional array is configured in polar coordinates, and the shift evaluation is performed in polar coordinates along at least one dimension.

3. The apparatus according to claim 2, wherein the detected motion corresponds to at least one of a rotational movement and a vasomotion.

4. The apparatus according to claim 3, wherein:

the rotational movement corresponds to at least one of a global rotational movement, a rigid rotational movement, and a local rotational movement, and the vasomotion corresponds to at least one of a global vasomotion and a local vasomotion.

5. The apparatus according to claim 3, further comprising an arrangement for stabilizing the second image in relation to the first image for at least one of the rotational movement and the vasomotion, wherein the stabilizing performed by the arrangement for stabilizing is performed in polar coordinates.

6. The apparatus according to claim 5, wherein the arrangement for stabilizing stabilizes at least one of a global rotation, a rigid rotation, a local rotation, a local vasomotion, and a global vasomotion.

7. The apparatus according to claim 6, wherein the arrangement for stabilizing at least one of the global rotation and the rigid rotation and the global vasomotion includes an arrangement for shifting the second image in polar coordinates along at least one dimension according to a magnitude and a direction derived from a result of the shift evaluation.

8. The apparatus according to claim 7, further comprising an arrangement for limiting a drift occurring due to the stabilizing of the second image in relation to the first image.

9. The apparatus according to claim 8, wherein the arrangement for limiting the drift includes an arrangement for shifting the second image by a magnitude that is adjusted by using information derived from a cardiovascular periodicity monitoring.

10. The apparatus according to claim 5, wherein the arrangement for performing the shift evaluation and detection operation includes:

an arrangement for providing a first complex two dimensional array having a first plurality of complex elements by applying a two dimensional Fourier transform to the first two dimensional array, an arrangement for providing a second complex two dimensional array having a second plurality of complex elements by applying a two dimensional Fourier transform to the second two dimensional array, an arrangement for obtaining a conjugate of the second plurality of elements, an arrangement for multiplying each one of the first plurality of complex elements with a corresponding one of the conjugate of the second plurality of complex elements, an arrangement for providing a result of each multiplication in a third two dimensional array, each complex data element of the third complex two dimensional array being a product of a multiplication between an element of the first complex two dimensional array and a corresponding conjugate element of the second complex two dimensional array, an arrangement for performing an inverse two dimensional Fourier transform on the third complex two dimensional array, an arrangement for obtaining a real component from each element of the inverse Fourier transformed third complex two dimensional array, an arrangement for providing each obtained real component in a fourth two dimensional array, and an arrangement for finding a location of a global maximum of the fourth two dimensional array, wherein the magnitude and the direction of at least one of the rigid rotation and the global vasomotion are indicated by the location of the global maximum along at least one of a first axis and a second axis of the fourth two dimensional array.

11. The apparatus according to claim 1, wherein the arrangement for performing the shift evaluation includes an arrangement for performing at least one closeness operation.

12. The apparatus according to claim 1, wherein:

each one of the first two dimensional array and the second two dimensional array is configured in Cartesian coordinates, and the shift evaluation is performed in Cartesian coordinates along at least one dimension.

13. The apparatus according to claim 12, wherein the detected motion corresponds to a Cartesian displacement.

14. The apparatus according to claim 13, wherein the Cartesian displacement corresponds to at least one of a rigid Cartesian displacement and a local Cartesian displacement.

15. The apparatus according to claim 13, further comprising an arrangement for stabilizing the second image in relation to the first image for the Cartesian displacement, wherein the stabilizing is performed in Cartesian coordinates.

16. The apparatus according to claim 15, further comprising an arrangement for displaying the first image and the stabilized second image.

17. The apparatus according to claim 15, wherein:

the Cartesian displacement includes one of a global Cartesian displacement, a local Cartesian displacement, and a rigid Cartesian displacement, and the arrangement for stabilizing includes an arrangement for stabilizing at least one of the global Cartesian displacement, the rigid Cartesian displacement, and the local Cartesian displacement.

18. The apparatus according to claim 17, wherein the arrangement for stabilizing at least one of the global Cartesian displacement and the rigid Cartesian displacement includes an arrangement for shifting the second image in Cartesian coordinates along at least one dimension according to a magnitude and a direction derived from a result of the shift evaluation.

19. The apparatus according to claim 18, further comprising an arrangement for limiting a drift occurring due to the stabilizing of the second image in relation to the first image.

20. The apparatus according to claim 19, wherein the arrangement for limiting the drift includes an arrangement for shifting the second image by a magnitude that is adjusted by using information derived from a cardiovascular periodicity monitoring.

21. An apparatus for performing an intravascular ultrasound imaging via an ultrasound signal transmitter and detector capable of being placed within a bodily lumen, comprising:

an arrangement for detecting a plurality of ultrasound signals;

an arrangement for deriving successive sets of ultrasound signals from the plurality of ultrasound signals;

an arrangement for deriving a plurality of successive images from the successive sets of ultrasound signals; and an arrangement for monitoring for a change in corresponding pixel values belonging to successive images in the plurality of images.

22. The arrangement according to claim 21, further comprising an arrangement for performing an image enhancement by filtering the change in the corresponding pixel values.

23. The arrangement according to claim 21, further comprising:

an arrangement for monitoring for a change in a texture of the corresponding pixel values; and an arrangement for performing an automatic image segmentation including a lumen identification.

24. An apparatus for performing an intravascular ultrasound imaging via an ultrasound signal transmitter and detector capable of being placed within a bodily lumen, comprising:

an arrangement for detecting a plurality of ultrasound signals;

an arrangement for deriving successive sets of ultrasound signals from the plurality of ultrasound signals;

an arrangement for deriving a plurality of successive images from the successive sets of ultrasound signals;

an arrangement for evaluating each pair of successive images; and an arrangement for deriving a closeness function, wherein:

for each pair of successive images, the arrangement for evaluating includes an arrangement for performing a closeness operation between a first image of the pair of images and a second image of the pair of images, and each value of the closeness function is a result of the performed closeness operation.

25. The arrangement according to claim 24, wherein the closeness operation corresponds to at least one of cross-correlation, normalized cross-correlation and SAD.

26. An apparatus for performing an intravascular ultrasound imaging via an ultrasound signal transmitter and detector capable of being placed within a bodily lumen, comprising:

an arrangement for detecting a plurality of ultrasound signals;

an arrangement for deriving successive sets of ultrasound signals from the plurality of ultrasound signals;

an arrangement for deriving a plurality of successive images from the successive sets of ultrasound signals; and an arrangement for performing a shift evaluation for each image in relation to a predecessor image in order to monitor each one of the successive images for a vasomotion of the bodily lumen.

27. The apparatus according to claim 26, wherein the vasomotion corresponds to at least one of a local vasomotion and a global vasomotion.

28. The apparatus according to claim 24, wherein the closeness function is monitored for cardiovascular periodicity.

29. The apparatus according to claim 28, wherein the monitoring of the closeness function includes at least one of a threshold crossing, an internal closeness function, a Fourier transform, and a spectral analysis.

30. The apparatus according to claim 24, wherein the closeness function is analyzed for indicating a quality of at least one image of the plurality of successive images used to form the closeness function.

31. The apparatus according to claim 24, wherein, for each pair of successive images, the arrangement for evaluating further includes an arrangement for performing a shift evaluation between the first image of the pair of images and the second image of the pair of images.

32. An apparatus for performing an intravascular ultrasound imaging via an ultrasound signal transmitter and detector capable of being placed within a bodily lumen, comprising:

an arrangement for detecting a plurality of ultrasound signals;

an arrangement for deriving a plurality of images from the plurality of detected ultrasound signals;

an arrangement for performing a shift evaluation for each image in relation to a predecessor image;

an arrangement for monitoring for a change in corresponding pixel values belonging to successive images in the plurality of images;

an arrangement for monitoring cardiovascular periodicity; and an arrangement for stabilizing each image of the plurality of images in relation to the predecessor image.

33. An apparatus for performing an intravascular ultrasound imaging via an ultrasound signal transmitter and detector capable of being placed within a bodily lumen, comprising:

an arrangement for moving the ultrasound signal transmitter and detector through a section of the bodily vessel;

an arrangement for detecting ultrasound signals;

an arrangement for deriving a first image from ultrasound signals detected during a first movement of the ultrasound signal transmitter and detector through the vessel;

an arrangement for deriving a second image from ultrasound signals detected during a second movement of the ultrasound signal transmitter and detector through the vessel;

an arrangement for performing a shift evaluation and a stabilization on the second image in relation to the first image; and an arrangement for displaying the stabilized second image.

34. An apparatus for performing an intravascular ultrasound imaging via an ultrasound signal transmitter and detector capable of being placed within a bodily lumen, comprising:

an arrangement for moving the ultrasound signal transmitter and detector through a section of the bodily vessel;

an arrangement for detecting ultrasound signals;

an arrangement for deriving a first image from ultrasound signals detected from a first portion of the vessel;

an arrangement for deriving a second image from ultrasound signals detected from a second portion of the vessel;

an arrangement for performing a shift evaluation and a stabilization on the second image in relation to the first image; and an arrangement for displaying the stabilized second image.

35. An apparatus for performing an intravascular ultrasound imaging via an ultrasound transmitter and detector capable of being placed within a bodily lumen, comprising:

an arrangement for performing a first movement of the ultrasound signal transmitter and detector along a first section of the vessel;

an arrangement for detecting a first set of ultrasound signals;

an arrangement for deriving a first series of successive images from the first set of detected ultrasound signals;

an arrangement for performing a second movement of the ultrasound signal transmitter and detector along a second section of the vessel;

an arrangement for detecting a second set of ultrasound signals;

an arrangement for deriving a second series of successive images from the second set of detected ultrasound signals;

an arrangement for selecting from the second series of successive images a subgroup of successive images formed as a reference segment;

an arrangement for performing a closeness operation between each image of the reference segment and each image of a plurality of subgroups of images derived from the first series of successive images; and an arrangement for matching each image of the reference segment to each image of another subgroup of the plurality of subgroups, the other subgroup being a matched segment.

36. The apparatus according to claim 35, wherein:

each image of the reference segment is associated by the arrangement for with a counterpart image from the matched segment, and each image of the reference segment covers substantially the same predetermined location of the vessel as the associated counterpart image.

37. The apparatus according to claim 36, further comprising an arrangement for stabilizing each image of the reference segment in relation to each counterpart image of the matched segment.

38. The apparatus according to claim 35, wherein the arrangement for matching includes an arrangement for performing a relative shift of the reference segment by at least a single image in relation to the first series of successive images, wherein each shift results in closeness operations being performed between images of a new subgroup of the plurality of subgroups derived from the first series of successive images and between the images of the reference segment.

39. The apparatus according to claim 38, wherein the arrangement for matching includes an arrangement for stabilizing each image of the reference segment in relation to each counterpart image of the new subgroup.

40. The apparatus according to claim 35, further comprising an arrangement for stabilizing each image of the second series of successive images in relation to each counterpart image of the first series of successive images.

41. The apparatus according to claim 35, wherein the closeness operation includes one of cross-correlation and normalized cross-correlation.

42. An apparatus for performing an IVUS imaging operation via an ultrasound transmitter and detector capable of being placed within a bodily lumen, comprising:

an arrangement for detecting a plurality of ultrasound signals reflected from at least a portion of the bodily lumen;

an arrangement for processing and digitizing a first set of ultrasound signals obtained from the plurality of reflected ultrasound signals in order to produce at least a first set of digitized samples and a second set of digitized samples;

an arrangement for deriving from the first set of digitized samples a first two dimensional array including a set of data, wherein:

the first two dimensional array includes a first plurality of elements, each of the first plurality of elements representing a digitized sample corresponding to one of the plurality of reflected ultrasound signals from a predetermined spatial location of the bodily lumen, the set of data of the first two dimensional array representing a complete cross section of the bodily lumen, the first two dimensional array is configured in polar coordinates, a first axis of the first two dimensional array represents an r coordinate, and a second axis of the first two dimensional array represents an angular coordinate;

an arrangement for deriving from the second set of digitized samples a second two dimensional array including a set of data, wherein:

the second two dimensional array includes a second plurality of elements, each of the second plurality of elements representing a digitized sample corresponding to one of the plurality of reflected ultrasound signals from the predetermined spatial location, the set of data of the second two dimensional array represents the complete cross section of the bodily lumen, the second two dimensional array is configured in polar coordinates, a first axis of the second two dimensional array represents the r coordinate, a second axis of the second two dimensional array axis represents the angular coordinate;

an arrangement for performing a shift evaluation and detection operation of the second two dimensional array with respect to the first two dimensional array in order to detect a magnitude and a direction of at least one of a global vasomotion and a rigid rotation represented by the set of data corresponding to the second two dimensional array in relation to the set of data corresponding to the first two dimensional array; and an arrangement for stabilizing the second two dimensional array by applying a shift having a selected magnitude and a selected direction to the second two dimensional array in order to uniformly shift along at least one of the first axis and the second axis of the second two dimensional array each of the second plurality of elements according to the selected magnitude and the selected direction, the stabilizing arrangement providing a compensation for at least one of the rigid rotation and the global vasomotion, wherein the selected magnitude and the selected shift direction are derived from the shift evaluation and detection operation.

43. The apparatus according to claim 42, wherein the arrangement for performing the shift evaluation and detection operation includes:

a) an arrangement for uniformly shifting each element of the second two dimensional array along the first axis of the second two dimensional array by a first predetermined magnitude in a first predetermined direction, b) an arrangement for uniformly shifting each element of the second two dimensional array along the second axis of the second two dimensional array by a second predetermined magnitude in a second predetermined direction, c) an arrangement for performing a closeness operation between corresponding elements of the shifted second two dimensional array and the first two dimensional array, d) an arrangement for providing the value resulting from the closeness operation as an element of a third two dimensional array, and e) an arrangement for repeating an operation of elements (a) to (d), each repetition being performed by shifting each element of the second two dimensional array along the first axis by a new first magnitude in a new first direction and along the second axis by a new second magnitude in a new second direction, until a location of a global extremum of all possible values of the third two dimensional array is established, wherein the magnitude and the direction of at least one of the rigid rotation and the global vasomotion are indicated by the location of the global extremum along at least one of a first axis and a second axis of the third two dimensional array.

44. The apparatus according to claim 43, further comprising:
an arrangement for reducing the number of repetitions of the operation of elements (a) to (d) in accordance with a performance of at least one of the following:
before the operation of element a), performing a sampling operation of the first two dimensional array and the second two dimensional array, and
initiating a search of the global extremum of the third two dimensional array, with each initial magnitude of the shift along the first axis and along the second axis of the second two dimensional array being equal to zero, wherein a detected local extremum of the third two dimensional array corresponds to the global extremum of the third two dimensional array.

45. The apparatus according to claim 42, further comprising:
an arrangement for converting the first two dimensional array into a third two dimensional array including a set of data and configured in Cartesian coordinates, wherein:
a first axis of the third two dimensional array corresponds to an X coordinate, and
a second axis of the third two dimensional array corresponds to a Y coordinate;
an arrangement for converting the stabilized second two dimensional array into a fourth two dimensional array including a set of data configured in Cartesian coordinates, the fourth two dimensional array including a plurality of elements, a first axis of the fourth two dimensional array corresponding to the X coordinate, and a second axis of the fourth two dimensional array corresponding to the Y coordinate;
an arrangement for performing a shift evaluation and detection operation of the fourth two dimensional array with respect to the third two dimensional array in order to detect a magnitude and a direction of a rigid Cartesian displacement along at least one of the X coordinate and the Y coordinate represented by the set of data corresponding to the fourth two dimensional array in relation to the set of data corresponding to the third two dimensional array;
an arrangement for stabilizing the fourth two dimensional array by applying a shift having a selected magnitude and a selected direction to the fourth two dimensional array in order to uniformly shift along at least one of the X coordinate and the Y coordinate each of the plurality of elements of the fourth two dimensional array according to the selected magnitude and the selected direction, the producing arrangement providing a compensation for the rigid Cartesian displacement, wherein the selected magnitude and the selected shift direction are derived from the arrangement for performing the shift evaluation and detection operation of the fourth two dimensional array with respect to the third two dimensional array.

46. The apparatus according to claim 45, further comprising:
an arrangement for displaying an image corresponding to the third two dimensional array and an image corresponding to the stabilized fourth two dimensional array.

47. An apparatus for performing an IVUS imaging operation via an ultrasound transmitter and detector capable of being placed within a bodily lumen, comprising:
an arrangement for detecting a plurality of ultrasound signals reflected from at least a portion of the bodily lumen;
an arrangement for processing and digitizing a first set of ultrasound signals obtained from the plurality of reflected ultrasound signals in order to produce at least a first set of digitized samples and a second set of digitized samples;
an arrangement for deriving from the first set of digitized samples a first two dimensional array including a set of data, wherein:
the first two dimensional array includes a first plurality of elements, each of the first plurality of elements representing a digitized sample corresponding to one of the plurality of reflected ultrasound signals from a predetermined spatial location of the bodily lumen, the set of data of the first two dimensional array representing a complete cross section of the bodily lumen,
the first two dimensional array is configured in Cartesian coordinates,
a first axis of the first two dimensional array represents an X coordinate, and
a second axis of the first two dimensional array represents a Y coordinate;
an arrangement for deriving from the second set of digitized samples a second two dimensional array including a set of data, wherein:
the second two dimensional array includes a second plurality of elements, each of the second plurality of elements representing a digitized sample corresponding to one of the plurality of reflected ultrasound signals from the predetermined spatial location,
the set of data of the second two dimensional array represents the complete cross section of the bodily lumen,
the second two dimensional array is configured in Cartesian coordinates,
a first axis of the second two dimensional array represents the X coordinate, and
a second axis of the second two dimensional array axis represents the Y coordinate;
an arrangement for performing a shift evaluation and detection operation of the second two dimensional array with respect to the first two dimensional array in order to detect a magnitude and a direction of a rigid Cartesian displacement along at least one of the X coordinate and the Y coordinate represented by the set of data corresponding to the second two dimensional array in relation to the set of data corresponding to first two dimensional array; and
an arrangement for stabilizing the second two dimensional array by applying a shift having a selected magnitude and a selected direction to the second two dimensional array in order to uniformly shift along at least one of the first axis and the second axis of the second two dimensional array each of the second plurality of elements according to the selected magnitude and the selected direction, the stabilizing arrangement providing a compensation for the rigid Cartesian displacement, wherein the selected magnitude and the selected direction are derived from the shift evaluation and detection operation.

48. The apparatus according to claim 47, further comprising:
an arrangement for displaying an image corresponding to the first two dimensional array and an image corresponding to the stabilized second two dimensional array.

49. The apparatus according to claim 47, wherein the arrangement for performing the shift evaluation and detection operation includes:
an arrangement for providing a first complex two dimensional array having a first plurality of complex elements by applying a two dimensional Fourier transform to the first two dimensional array,
an arrangement for providing a second complex two dimensional array having a second plurality of complex elements by applying a two dimensional Fourier transform to the second two dimensional array,
an arrangement for obtaining a conjugate of the second plurality of elements, multiplying each one of the first plurality of complex elements with a corresponding one of the conjugate of the second plurality of complex elements,
an arrangement for providing a result of each multiplication in a third two dimensional array, wherein each complex data element of the third complex two dimensional array is a product of a multiplication between an element of the first complex two dimensional array and a corresponding conjugate element of the second complex two dimensional array,
an arrangement for performing an inverse two dimensional Fourier transform on the third complex two dimensional array,
an arrangement for obtaining a real component from each element of the inverse Fourier transformed third complex two dimensional array,
an arrangement for providing each obtained real component in a fourth two dimensional array, and
an arrangement for finding a location of a global maximum of the fourth two dimensional array, wherein the magnitude and the direction of the rigid Cartesian displacement along at least one of the X axis and the Y axis are indicated by the location of the global extremum along at least one of a first axis and a second axis of the fourth two dimensional array.

50. The apparatus according to claim 47, wherein the arrangement for performing the shift evaluation and detection operation includes:
a) an arrangement for uniformly shifting each element of the second two dimensional array along the first axis of the second two dimensional array by a first predetermined magnitude in a first predetermined direction,
b) an arrangement for uniformly shifting each element of the second two dimensional array along the second axis of the second two dimensional array by a second predetermined magnitude in a second predetermined direction,
c) an arrangement for performing a closeness operation between corresponding elements of the shifted second two dimensional array and the first two dimensional array,
d) an arrangement for providing the value resulting from the closeness operation as an element of a third two dimensional array, and
e) an arrangement for repeating an operation of elements (a) to (d), each repetition being performed by shifting each element of the second two dimensional array along the first axis by a new first magnitude in a new first direction and along the second axis by a new second magnitude in a new second direction, until a location of a global extremum of all possible values of the third two dimensional array is established, wherein the magnitude and the direction of the rigid Cartesian displacement along at least one of the X axis and the Y axis are indicated by the location of the global extremum along at least one of a first axis and one of a second axis of the third two dimensional array.

51. The apparatus according to claim 50, further comprising:
an arrangement for reducing the number of repetitions of the operation of elements (a) to (d) in accordance with a performance of at least one of:
before an operation of element a), performing a sampling operation of the first two dimensional array and the second two dimensional array, and
initiating a search of the global extremum of the third two dimensional array, with each initial magnitude of the shift along the first axis and along the second axis of the second two dimensional array being equal to zero, and wherein a detected local extremum of the third two dimensional array corresponds to the global extremum of the third two dimensional array.

52. An apparatus for forming and processing a closeness function via an ultrasound transmitter and detector capable of being placed within a bodily lumen in order to monitor a cardiovascular periodicity from an IVUS imaging operation, comprising:
an arrangement for detecting a plurality of ultrasound signals reflected from at least a portion of the bodily lumen;
an arrangement for processing and digitizing a first set of ultrasound signals obtained from the plurality of reflected ultrasound signals in order to produce at least a first plurality of successive frames, each frame including a set of data, wherein:
each frame includes a plurality of elements,
each one of the plurality of elements represents a digitized sample corresponding to one of the plurality of reflected ultrasound signals from a predetermined spatial location of the bodily lumen,
the set of data corresponding to each one of the plurality of frames representing a complete cross section of the bodily lumen, and
each one of the plurality of frames is configured in at least one of Cartesian coordinates and polar coordinates;
an arrangement for providing a one dimensional function formed as a closeness function, wherein a value of the closeness function corresponding to f(n), n being a positive integer, is determined by a closeness operation performed between elements stored in the nth frame and between elements stored in the nth+1 frame; and
an arrangement for processing the closeness function in order to derive a magnitude of a periodicity of the closeness function.

53. The apparatus according to claim 52, wherein:
the bodily lumen is a blood vessel, and
the magnitude of the periodicity of the closeness function corresponds to a magnitude of the cardiovascular periodicity.

54. The apparatus according to claim 53, wherein the magnitude of the cardiovascular periodicity enables performance of a cardiac gating operation with respect to a cardiovascular cycle.

55. The apparatus according to claim 52, wherein:
an image for display corresponds to one frame of the first plurality of frames used to form the closeness function, and
an absence of the periodicity of the closeness function indicates an existence of an artifact in the image for display.

56. The apparatus according to claim 55, wherein the artifact is caused by a non uniformity of a rotation of at least one of the ultrasound signal transmitter and the ultrasound signal detector within the bodily lumen.

57. An apparatus for automatically segmenting an IVUS image via an ultrasound transmitter and detector capable of being placed within a bodily lumen, comprising:
an arrangement for detecting a plurality of ultrasound signals reflected from at least a portion of the bodily lumen;
an arrangement for processing and digitizing a first set of ultrasound signals obtained from the plurality of reflected ultrasound signals in order to produce a plurality of sets of digitized samples;
an arrangement for deriving a plurality of successive frames from the plurality of sets of digitized samples, wherein:
each frame includes a plurality of pixels;
each pixel represents one of the plurality of digitized samples corresponding to one of the plurality of reflected ultrasound signals from a predetermined spatial location of the bodily lumen, each frame representing a complete cross section of the bodily lumen, and
each frame is configured in at least one of polar coordinates and Cartesian coordinates;
an arrangement for assigning one of a plurality of textural categories to each pixel included in each frame based on a relationship of each pixel with an adjacent pixel, each assigned textural category being derived from the corresponding pixel being one of higher than, lower than, and equal to in value with respect to each closest adjacent pixel;
an arrangement for detecting a change in the assigned textural category of each pixel by monitoring the textural category assigned to each pixel included in each one of the plurality of frames; and
an arrangement for producing a binary frame including:
an arrangement for classifying each pixel corresponding to a selected one of the plurality frames into one of a first class and a second class, and
an arrangement for assigning a binary value to each pixel corresponding to the selected frame, wherein the first class indicates an absence of a change in the textural category assigned to the associated pixel, and wherein the second class indicates a presence of a change in the textural category assigned to the associated pixel.

58. The apparatus according to claim 57, wherein:
the bodily lumen is a blood vessel, and
each pixel corresponding to each frame represents one of a blood flow through the blood vessel, a vessel tissue of the blood vessel, and an exterior tissue surrounding the blood vessel,
each pixel associated with the first class represents the vessel tissue, each pixel associated with the second class represents one of the blood flow and the exterior tissue, and
the binary frame is further processed in order to extract that region of pixels associated with the blood flow through the blood vessel in the selected frame.

59. An apparatus for enhancing a quality of an IVUS imaging operation via an ultrasound transmitter and detector capable of being placed within a bodily lumen, comprising:
an arrangement for detecting a plurality of ultrasound signals reflected from at least a portion of the bodily lumen;
an arrangement for processing and digitizing a first set of ultrasound signals obtained from the plurality of reflected ultrasound signals in order to produce a plurality of sets of digitized samples;
an arrangement for deriving a plurality of successive frames from the plurality of sets of digitized samples, wherein:
each frame includes a plurality of pixels,
each pixel represents one of the plurality of digitized samples corresponding to one of the plurality of reflected ultrasound signals from a predetermined spatial location of the bodily lumen, each frame representing a complete cross section of the bodily lumen, and
each frame is configured in at least one of polar coordinates and Cartesian coordinates;
an arrangement for deriving a first difference frame having a plurality of pixels, each pixel of the first difference frame including a pixel value, wherein each pixel value corresponds to a sum of absolute differences between pixels included in a first frame of the plurality of frames and between corresponding pixels included in a second frame of the plurality of frames;
an arrangement for deriving a second difference frame having a plurality of pixels, each pixel of the second difference frame including a pixel value, wherein each pixel value of each pixel of the second difference frame corresponds to the sum of absolute differences between pixels included in the second frame of the plurality of frames and between corresponding pixels included in a third frame of the plurality of frames;
an arrangement for deriving a maximum value frame having a plurality of pixels, each pixel of the maximum value frame including a pixel value, wherein each pixel value of each pixel of the maximum value frame corresponds to a maximum value selected between the pixel value of each pixel of the first difference frame and the pixel value of each corresponding pixel of the second difference frame;
an arrangement for deriving a first mask frame by applying a normalization operation to the maximum value frame, wherein the normalization operation includes an arrangement for dividing the pixel value of each pixel of the maximum value frame by the pixel value of the pixel in the maximum value frame having the highest pixel value in the maximum value frame;
an arrangement for deriving a second mask frame including:
an arrangement for raising each pixel value of the first mask frame to a power, and
an arrangement for subtracting each raised pixel value from the value of 1;
an arrangement for deriving an enhanced frame by multiplying each pixel value of a selected one of the plurality of frames by a corresponding pixel value of the second mask frame; and an arrangement for displaying an image corresponding to the enhanced frame.

60. The apparatus according to claim 59, wherein:

the bodily lumen is a blood vessel, each pixel corresponding to each frame of the plurality of frames represents one of a blood flow through the blood vessel, a vessel tissue of the blood vessel, and an exterior tissue surrounding the blood vessel, an appearance of the blood flow and an appearance of the exterior tissue in the image corresponding to the enhanced frame are suppressed, and an appearance of the vessel tissue is enhanced.

61. A apparatus for performing an automatic matching operation with respect to an IVUS imaging operation via an ultrasound transmitter and detector capable of being placed within a bodily lumen, comprising:

an arrangement for moving each of the ultrasound signal transmitter and the ultrasound signal detector along a length of a first segment of the bodily vessel;

an arrangement for detecting a first plurality of ultrasound signals reflected from at least a portion of the bodily vessel;

an arrangement for processing and digitizing a first set of ultrasound signals obtained from the first plurality of reflected ultrasound signals in order to produce a first plurality of sets of digitized samples;

an arrangement for deriving a first plurality of successive frames for a first pullback film from the first plurality of sets of digitized samples, wherein:

each frame includes a first plurality of elements, each element represents one of the first plurality of digitized samples corresponding to one of the first plurality of reflected ultrasound signals from a first predetermined spatial location of the bodily vessel, each frame representing a complete cross section of the bodily vessel, and each frame is configured in at least one of polar coordinates and Cartesian coordinates;

an arrangement for moving each of the ultrasound signal transmitter and the ultrasound signal detector along a length of a second segment of the bodily vessel, the second segment substantially overlapping the first segment;

an arrangement for detecting a second plurality of ultrasound signals reflected from at least a portion of the bodily vessel;

an arrangement for processing and digitizing a second set of ultrasound signals obtained from the second plurality of reflected ultrasound signals in order to produce a second plurality of sets of digitized samples;

an arrangement for deriving a second plurality of successive frames for a second pullback film from the second plurality of sets of digitized samples, wherein:

each frame of the second plurality of successive frames includes a second plurality of elements, each element of the second plurality of elements represents one of the second plurality of digitized samples corresponding to one of the second plurality of reflected ultrasound signals from a second predetermined spatial location of the bodily vessel, each frame of the second plurality of successive frames representing the complete cross section of the bodily vessel, and each frame of the second plurality of successive frames is configured in at least one of polar coordinates and Cartesian coordinates;

an arrangement for selecting as a reference segment a subset of successive frames from the second pullback film, the reference segment representing a section of the bodily vessel also represented by a subset of successive frames derived from the first pullback film and formed as a second segment; and an arrangement for automatically matching between the reference segment and the second segment by performing closeness operations between frames of the first pullback film and frames of the reference segment.

62. The apparatus according to claim 61, wherein:

the reference segment includes m successive frames, m being a positive integer, and the arrangement for automatically matching includes:

(a) an arrangement for selecting m successive frames from the first pullback film, (b) an arrangement for performing a closeness operation between each frame of the reference segment and each of the m frames selected by element (a) in order to produce m closeness values, (c) an arrangement for averaging the m closeness values onto a single value of a one dimensional closeness function, and (d) an arrangement for repeating an operation of elements (a) to (c), each repetition including a relative shift of the reference segment with respect to the first pullback film by at least one frame and each shift resulting in a selection of a new set of m successive frames in element (a), until a maximal value of the closeness function is indicative that a matching between the reference segment and the second segment has been accomplished.

63. The apparatus according to claim 62, further comprising:

an arrangement for, prior to a performance of the operation of element (b), stabilizing each of the frames of the reference segment with respect to a counterpart frame of the selected m successive frames in order to compensate for at least one of a rigid rotational motion and a rigid Cartesian displacement.

64. The apparatus according to claim 61, further comprising:

an arrangement for displaying the first pullback film synchronously with the second pullback film so that an image of the first pullback film displayed simultaneously with an image of the second pullback film both correspond to the same location along the bodily vessel.

65. The apparatus according to claim 61, further comprising:

an arrangement for removing from the bodily vessel the ultrasound signal transmitter and the ultrasound signal detector, and an arrangement for reinserting into the bodily vessel the ultrasound signal transmitter and the ultrasound signal detector in order to move each of the ultrasound signal transmitter and the ultrasound signal detector along the length of the second segment of the bodily vessel.

66. An apparatus for monitoring a local vasomotion of a blood vessel via an ultrasound transmitter and detector capable of being placed within a bodily lumen, comprising:

an arrangement for detecting a plurality of ultrasound signals reflected from at least a portion of the blood vessel;

an arrangement for processing and digitizing a first set of ultrasound signals obtained from the plurality of reflected ultrasound signals in order to produce at least a first set of digitized samples and a second set of digitized samples;

an arrangement for deriving from the first set of digitized samples a first two dimensional array including a set of data, wherein:
  the first two dimensional array includes a first plurality of elements, each of the first plurality of elements representing a digitized sample corresponding to one of the plurality of reflected ultrasound signals from a predetermined spatial location of the bodily vessel,
  the set of data of the first two dimensional array representing a complete cross section of the blood vessel,
  the first two dimensional array is configured in polar vectors,
  a first axis of the first two dimensional array represents an r coordinate, and
  a second axis of the first two dimensional array represents an angular coordinate;

an arrangement for deriving from the second set of digitized samples a second two dimensional array including a set of data, wherein:
  the second two dimensional array includes a second plurality of elements, each of the second plurality of elements representing a digitized sample corresponding to one of the plurality of reflected ultrasound signals from the predetermined spatial location,
  the set of data of the second two dimensional array represents the complete cross section of the blood vessel,
  the second two dimensional array is configured in polar vectors,
  a first axis of the second two dimensional array represents the r coordinate,
  a second axis of the second two dimensional array axis represents the angular coordinate; and an arrangement for detecting a magnitude and a direction of the local vasomotion by applying a plurality of one dimensional shifts on the set of data of each polar vector of the second two dimensional array and by applying a closeness operation between the shifted set of data of each polar vector of the second two dimensional array and between the set of data of each corresponding polar vector of the first two dimensional array.

67. The apparatus according to claim 66, wherein the detection of the local vasomotion results in a local vasomotion value for each polar vector of the second two dimensional array, and wherein the apparatus further comprises an arrangement for averaging each local vasomotion value in order to produce a single average vasomotion value for the second two dimensional array, the single average vasomotion value indicating a global vasomotion.

68. The apparatus according to claim 67, further comprising:
  an arrangement for continuously producing additional two dimensional arrays;
  an arrangement for detecting and averaging additional local vasomotion values in each additional two dimensional array in order to produce an additional single average vasomotion value for each additional two dimensional array; and
  an arrangement for displaying each additional single average vasomotion value together as a vasomotion curve.

* * * * *